US012635968B2

(12) United States Patent
Kim et al.

(10) Patent No.: US 12,635,968 B2
(45) Date of Patent: May 26, 2026

(54) RADIOGRAPHIC IMAGING APPARATUS FOR OBTAINING IMPROVED RADIOGRAPHIC IMAGES AND OPERATION METHOD THEREOF

(71) Applicant: DRTECH CORPORATION, Seongnam-si (KR)

(72) Inventors: Hyun Jong Kim, Suwon-si (KR); Choul Woo Shin, Seongnam-si (KR); Il Woong Choi, Seoul (KR)

(73) Assignee: DRTECH CORPORATION, Seongnam-si (KR)

( * ) Notice: Subject to any disclaimer, the term of this patent is extended or adjusted under 35 U.S.C. 154(b) by 143 days.

(21) Appl. No.: 18/762,765

(22) Filed: Jul. 3, 2024

(65) Prior Publication Data

US 2024/0389965 A1      Nov. 28, 2024

Related U.S. Application Data

(63) Continuation of application No. PCT/KR2024/095796, filed on May 17, 2024.

(30) Foreign Application Priority Data

May 22, 2023      (KR) ........................ 10-2023-0065377

(51) Int. Cl.
*A61B 6/00*              (2024.01)
(52) U.S. Cl.
CPC .............. *A61B 6/542* (2013.01); *A61B 6/488* (2013.01)
(58) Field of Classification Search
CPC ....... A61B 6/4441; A61B 6/487; A61B 6/488; A61B 6/542
See application file for complete search history.

(56) References Cited

U.S. PATENT DOCUMENTS 5,574,764 A      11/1996   Granfors et al.
6,295,336 B1 *    9/2001   Aach .................... A61B 6/5211
                                                                   378/98.7
(Continued)

FOREIGN PATENT DOCUMENTS

CN          105342630 A      2/2016
JP          2007029161 A     2/2007
(Continued)

OTHER PUBLICATIONS

Korean Office Action for KR 10-2023-0065377 dated May 29, 2025.
Extended European Search Report for EP 24735850.0 dated Feb. 2, 2026.

*Primary Examiner* — Dani Fox
(74) *Attorney, Agent, or Firm* — Dinsmore & Shohl LLP; Yongsok Choi, Esq.

(57) ABSTRACT

A radiographic imaging apparatus of the present disclosure includes an image outputter outputting a first radiographic image included in continuous radiographic images obtained by radiographic imaging of a subject, an image brightness information extractor obtaining brightness information from the first radiographic image, a first irradiation condition calculator determining a first irradiation condition based on the brightness information, an irradiation controller controlling a radiation dose based on the first irradiation condition, a second irradiation condition calculator determining a second irradiation condition based on a second radiographic image generated based on the first irradiation condition when an imaging site of the subject is fixed, and a dose reducer reducing or maintaining the radiation dose based on the second irradiation condition.

16 Claims, 12 Drawing Sheets

(56) References Cited

U.S. PATENT DOCUMENTS

| 6,647,093 | B2 | 11/2003 | Schmitz et al. |
| 2018/0333124 | A1 | 11/2018 | Kaneko |
| 2019/0223278 | A1 | 7/2019 | Jordan et al. |
| 2021/0017163 | A1 | 1/2021 | Kuntz |

FOREIGN PATENT DOCUMENTS

| JP | 2010273834 | A | 12/2010 |
| JP | 2018114190 | A | 7/2018 |

* cited by examiner

FIG. 3

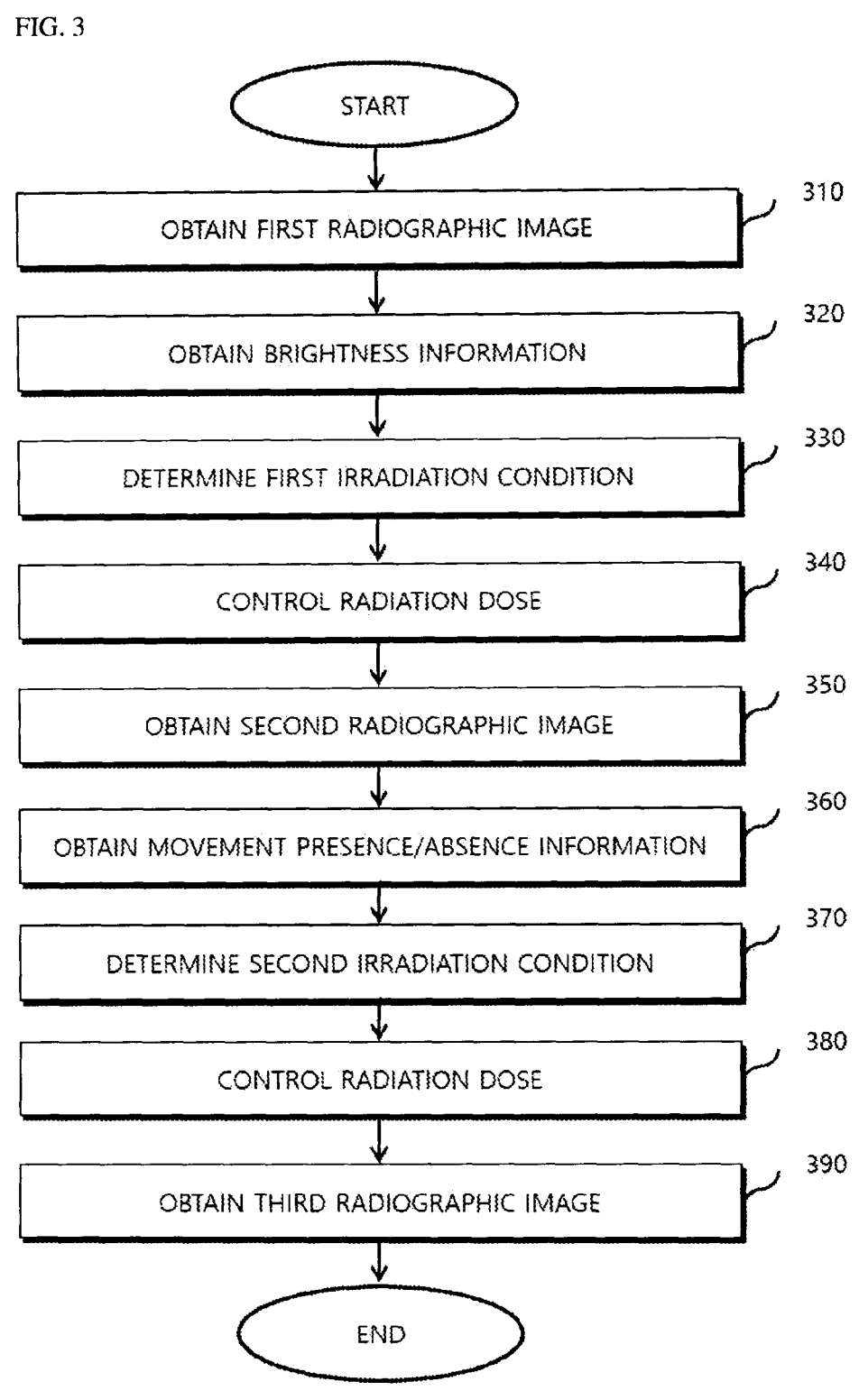

```
                        ┌─────────────┐
                        │    START    │
                        └──────┬──────┘
                               ▼
        ┌──────────────────────────────────────────┐
        │     OBTAIN FIRST RADIOGRAPHIC IMAGE       │⟞ 310
        └──────────────────────┬───────────────────┘
                               ▼
        ┌──────────────────────────────────────────┐
        │       OBTAIN BRIGHTNESS INFORMATION       │⟞ 320
        └──────────────────────┬───────────────────┘
                               ▼
        ┌──────────────────────────────────────────┐
        │    DETERMINE FIRST IRRADIATION CONDITION  │⟞ 330
        └──────────────────────┬───────────────────┘
                               ▼
        ┌──────────────────────────────────────────┐
        │          CONTROL RADIATION DOSE           │⟞ 340
        └──────────────────────┬───────────────────┘
                               ▼
        ┌──────────────────────────────────────────┐
        │     OBTAIN SECOND RADIOGRAPHIC IMAGE      │⟞ 350
        └──────────────────────┬───────────────────┘
                               ▼
        ┌──────────────────────────────────────────┐
        │ OBTAIN MOVEMENT PRESENCE/ABSENCE INFORMATION │⟞ 360
        └──────────────────────┬───────────────────┘
                               ▼
        ┌──────────────────────────────────────────┐
        │  DETERMINE SECOND IRRADIATION CONDITION   │⟞ 370
        └──────────────────────┬───────────────────┘
                               ▼
        ┌──────────────────────────────────────────┐
        │          CONTROL RADIATION DOSE           │⟞ 380
        └──────────────────────┬───────────────────┘
                               ▼
        ┌──────────────────────────────────────────┐
        │     OBTAIN THIRD RADIOGRAPHIC IMAGE       │⟞ 390
        └──────────────────────┬───────────────────┘
                               ▼
                        ┌─────────────┐
                        │     END     │
                        └─────────────┘
```

RADIOGRAPHIC IMAGING APPARATUS FOR OBTAINING IMPROVED RADIOGRAPHIC IMAGES AND OPERATION METHOD THEREOF

CROSS-REFERENCE TO RELATED APPLICATIONS

This application is a continuation of International Application No. PCT/KR2024/095796 filed on May 17, 2024, which claims priority to Korean Patent Application No. 10-2023-0065377 filed on May 22, 2023, the entire contents of which are herein incorporated by reference.

TECHNICAL FIELD

The present disclosure relates to a radiographic imaging apparatus for obtaining improved radiographic images and an operation method thereof. The radiographic imaging apparatus determines irradiation conditions using different methods when obtaining continuous radiographic images.

BACKGROUND ART

Radiographic imaging apparatuses that implement low-dose imaging reduce a risk of side effects, and thus the importance thereof is gradually increasing in medical imaging. Such apparatuses can achieve low-dose imaging using an advanced software algorithm, an improved hardware component, and a new type of radiation source.

Radiographic imaging apparatuses that achieve low-dose imaging have limitations in that they may generate images with reduced contrast and spatial resolution. Thus, it may become more difficult to detect small lesions or abnormalities. Also, low-dose imaging may not be suitable for a specific type of imaging procedure that requires high-dose imaging for visualizing a specific structure or abnormal sign.

Also, low-dose radiographic imaging apparatuses are relatively expensive, and thus accessibility thereto may be limited. Further, additional training and expertise of radiographers and radiologists may be necessary to implement new technology and techniques, and thus there is difficulty in employing the low-dose imaging apparatuses.

Among low-dose radiographic imaging apparatuses, one radiographic imaging apparatus that is widely known is equipment that continuously irradiates an affected area of a human body or animal body with X-rays to obtain a fluoroscopic image of the affected area in real time for use in surgery or treatment. When the radiographic imaging apparatus is used to perform surgery on a patient, there is a problem in that it is not possible to maintain constant brightness and quality of images because irradiation conditions and image brightness are affected by objects other than an object of interest, such as an operator's hand and a surgical tool. Also, since the conventional automatic irradiation condition adjustment method uses irradiation conditions that may be used for various subjects, a subject actually being imaged may be irradiated with a dose of radiation higher than an appropriate irradiation dose.

Despite such limitations, due to an aspect that a risk of side effects can be reduced and patient safety can be improved by minimizing exposure to radiation, there is demand for using low-dose radiographic imaging apparatuses in medical imaging. Therefore, much research on implementing low-dose radiographic imaging apparatuses is underway.

SUMMARY

Technical Problem

The present disclosure discloses a radiographic imaging apparatus implementing a low-dose radiographic image. More specifically, the radiographic imaging apparatus rapidly obtains a low-dose radiographic image to minimize a burden on the patient and the user.

Technical Solution

A radiographic imaging apparatus according to the present disclosure includes an image outputter outputting a first radiographic image included in continuous radiographic images obtained by radiographic imaging of a subject, an image brightness information extractor obtaining brightness information from the first radiographic image, a first irradiation condition calculator determining a first irradiation condition based on the brightness information, an irradiation controller controlling a radiation dose based on the first irradiation condition, a second irradiation condition calculator determining a second irradiation condition based on a second radiographic image generated based on the first irradiation condition when an imaging site of the subject is fixed, and a dose reducer reducing or maintaining the radiation dose based on the second irradiation condition.

A value resulting from subtracting the radiation dose based on the second irradiation condition from the radiation dose based on the first irradiation condition of the radiographic imaging apparatus according to the present disclosure may be less than or equal to 70% of the dose based on the first irradiation condition.

The radiographic imaging apparatus according to the present disclosure may deactivate the first irradiation condition calculator when the dose is reduced by the dose reducer.

The radiographic imaging apparatus according to the present disclosure may generate an improved current frame image by accumulating and averaging pixel values included in a current frame image included in a third radiographic image output using the dose reduced by the dose reducer and a previous frame image included in the third radiographic image.

The radiographic imaging apparatus according to the present disclosure may further include an image postprocessor postprocessing the third radiographic image output using the dose reduced by the dose reducer, and the image postprocessor may adjust at least one of brightness information and contrast information of the third radiographic image to be similar to at least one of brightness information and contrast information of the second radiographic image.

A radiographic imaging apparatus according to the present disclosure includes a radiation irradiator irradiating a subject with radiation, an image obtainer generating continuous radiographic images by receiving the radiation radiated from the radiation irradiator and passing through the subject, and a controller controlling the radiation irradiator and the image obtainer, and an operation method of the radiographic imaging apparatus includes, by the controller, obtaining brightness information based on a first radiographic image included in the continuous radiographic images, determining a first irradiation condition based on the brightness information according to a first algorithm, controlling a radiation dose based on the first irradiation condition, obtaining a second radiographic image included in the continuous radiographic images and generated based on the first irradiation condition, obtaining movement presence/absence information indicating whether an imaging site of the subject is fixed, determining a second irradiation condition based on the second radiographic image according to a second algorithm when the movement presence/absence information indicates that the imaging site of the subject is fixed, controlling the radiation dose based on the second irradiation condition, and obtaining a third radiographic image included in the continuous radiographic images and generated based on the second irradiation condition.

The radiation dose based on the second irradiation condition of the operation method of the radiographic imaging apparatus according to the present disclosure may be greater than or equal to 30% of the radiation dose based on the first irradiation condition.

The first algorithm determining the first irradiation condition and the second algorithm determining the second irradiation condition of the operation method of the radiographic imaging apparatus according to the present disclosure may be different from each other.

The obtaining of the third radiographic image of the operation method of the radiographic imaging apparatus according to the present disclosure may include generating an improved current frame image by accumulating and averaging pixel values included in at least a part of a current frame image included in the third radiographic image and pixel values included in at least a part of a previous frame image included in the third radiographic image.

The obtaining of the third radiographic image of the operation method of the radiographic imaging apparatus according to the present disclosure may include generating a movement detection image including movement detection information on each pixel of a differential image obtained from a differential of a current frame image included in the third radiographic image and a previous frame image included in the third radiographic image, generating a movement probability image based on the generated movement detection image and a movement detection image accumulated up to a previous frame, and generating an improved current frame image by mixing the current frame image and the previous frame image based on the movement probability image.

The generating of the movement probability image of the operation method of the radiographic imaging apparatus according to the present disclosure may include generating the movement probability image from a sum of a movement detection image of a current frame and one or more movement detection images up to the previous frame, the generating of the improved current frame image may include variably determining a mixing ratio of the current frame image and the previous frame image according to a value indicating a degree of movement of each pixel of the movement probability image, and the mixing ratio may be determined for a reflection rate of the current frame image relative to the previous frame image to increase as the degree of movement indicated by the value of each pixel of the movement probability image is higher.

The obtaining of the brightness information of the operation method of the radiographic imaging apparatus according to the present disclosure may include obtaining the brightness information by averaging pixel values included in at least a part of the first radiographic image, and the determining of the first irradiation condition may include determining the first irradiation condition for the brightness information to increase when the brightness information is less than predetermined first threshold brightness information and determining the first irradiation condition for the brightness information to decrease when the brightness information is greater than the predetermined first threshold brightness information.

The obtaining of the brightness information by averaging the pixel values included in at least a part of the first radiographic image of the operation method of the radiographic imaging apparatus according to the present disclosure may include obtaining a region showing the subject from the first radiographic image based on a subject region obtaining model and obtaining brightness information by averaging pixel values included in the region showing the subject.

The determining of the second irradiation condition of the operation method of the radiographic imaging apparatus according to the present disclosure may include obtaining a downsampled image by downsampling the second radiographic image into units of patches of a predetermined size, obtaining a minimum pixel value among pixel values included in the downsampled image, and determining the second irradiation condition for the minimum pixel value to become equal to predetermined second threshold brightness information when the minimum pixel value is greater than the second threshold brightness information.

The determining of the second irradiation condition for the minimum pixel value to become equal to the second threshold brightness information of the operation method of the radiographic imaging apparatus according to the present disclosure may include determining a reduction rate based on the minimum pixel value and the second threshold brightness information and determining the second irradiation condition for the radiation irradiator to radiate radiation with a dose resulting from subtracting a value obtained by multiplying the dose based on the first irradiation condition by the reduction rate from the dose based on the first irradiation condition, and the reduction rate may be greater than 0 and less than a predetermined maximum reduction rate.

The obtaining of the movement presence/absence information of the operation method of the radiographic imaging apparatus according to the present disclosure may include determining the movement presence/absence information to indicate that the imaging site of the subject is not fixed when less than a predetermined threshold amount of time is passed from a time at which at least one of the first radiographic image and the second radiographic image is obtained and determining the movement presence/absence information to indicate that the imaging site of the subject is fixed when the predetermined threshold amount of time or more is passed from the time at which at least one of the first radiographic image and the second radiographic image is obtained.

Also, a program for implementing the operation method of the radiographic imaging apparatus described above may be recorded in computer-readable recording media.

Advantageous Effects

A radiographic imaging apparatus of the present disclosure can explicitly fix image brightness to address the above-described problems. Also, when an imaging site is determined as having been fixed, the radiographic imaging apparatus can reduce a radiation dose of a patient using an irradiation condition optimized for the corresponding site.

The radiographic imaging apparatus of the present disclosure can minimize radiation exposure of a patient and a user by obtaining a low-dose radiographic image. Also, the radiographic imaging apparatus of the present disclosure can assist the user in making a medical judgment by providing a low-dose image with high sharpness to the user. Also, the radiographic imaging apparatus of the present disclosure can rapidly obtain a low-dose radiographic image by minimizing image processing and thus assist the user in promptly performing medical treatment.

DESCRIPTION OF DRAWINGS

FIG. 3 is a flowchart illustrating an operation method of the radiographic imaging apparatus according to one embodiment of the present disclosure.

DETAILED DESCRIPTION

Figure 1:
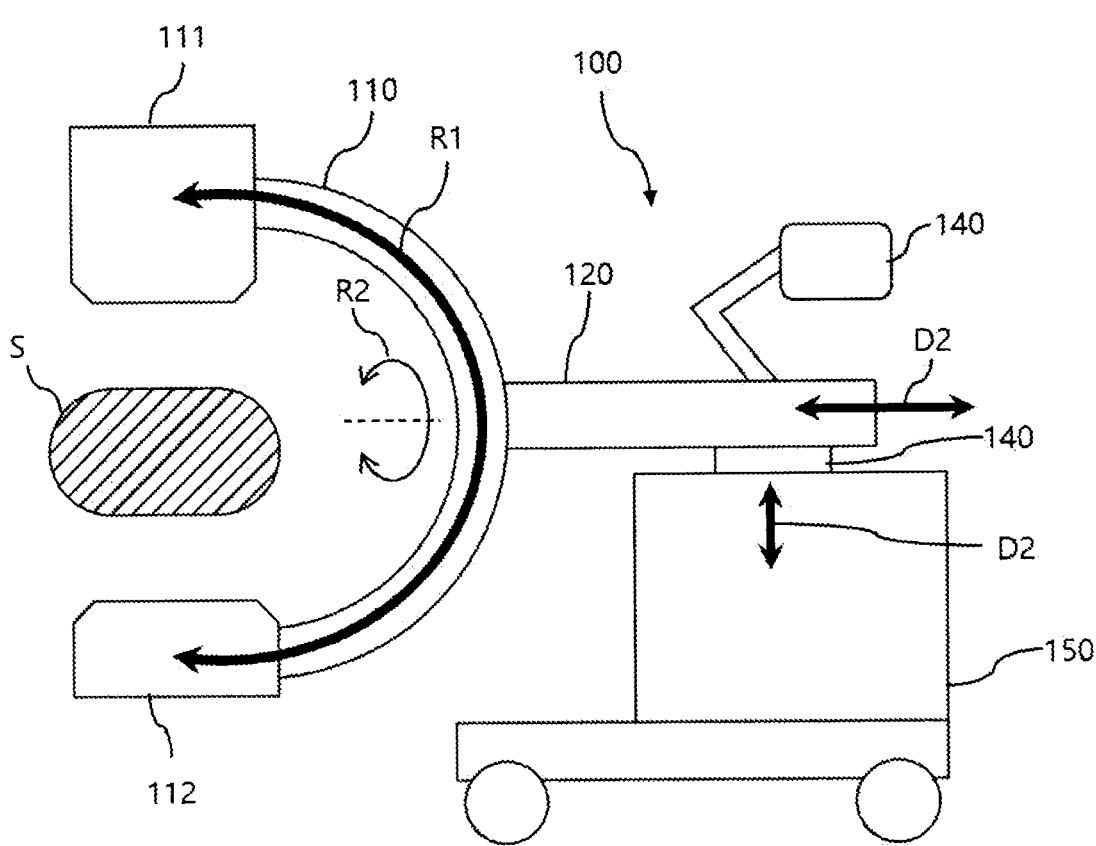
FIG. 1 is a view illustrating a movable radiographic imaging apparatus according to one embodiment of the present disclosure.

Advantages and features of the embodiments disclosed herein and methods of achieving the same should become clear from embodiments described in detail below with reference to the accompanying drawings. However, the present disclosure is not limited to the embodiments disclosed below and may be implemented in various different forms. The present embodiments are only provided to make the present disclosure complete and completely inform those of ordinary skill in the art to which the present disclosure pertains of the scope of the invention.

Terms used in the present specification will be briefly described, and embodiments disclosed herein will be described in detail.

General terms that are currently widely used have been selected as terms used in the present specification in consideration of functions in the present disclosure, but the terms may be changed according to an intention or practice of those of ordinary skill in the art, the advent of new technology, and the like. Also, in some cases, some terms may have been arbitrarily selected by the applicant, and in such cases, the meanings of the terms will be described in detail in the corresponding part of the description of the invention. Therefore, the terms used in the present disclosure should be defined based on the meanings of the terms and the content throughout the present disclosure, instead of being simply defined based on the names of the terms.

In the present specification, a singular expression includes a plural expression unless the context clearly indicates singularity. Also, a plural expression includes a singular expression unless the context clearly indicates plurality.

Throughout the specification, when a certain part is described as "including" a certain component, this indicates that the certain part may further include other components instead of excluding other components unless the context clearly indicates otherwise.

Also, the term "-er/-or" or "part" used in the specification refers to a software or hardware component, and an "-er/-or" or "part" performs certain roles. However, the meaning of "-er/-or" or "part" is not limited to software or hardware. An "-er/-or" or "part" may be configured to be present in addressable storage media or configured to replay one or more processors. Therefore, as one example, an "-er/-or" or "part" may include components such as software components, object-oriented software components, class components, and task components, processes, functions, attributes, procedures, subroutines, program code segments, drivers, firmware, micro codes, circuits, data, databases, data structures, tables, arrays, or variables. The components and functions provided in "-ers/-ors" or "parts" may be combined into smaller numbers of components and "-ers/-ors" or "parts" or may be further separated into larger numbers of components and "-ers/-ors" or "parts."

According to one embodiment of the present disclosure, an "-er/-or" or "part" may be implemented using a processor and a memory. The term "processor" should be interpreted in a wide sense to include a universal processor, a central processing unit (CPU), a microprocessor, a digital signal processor (DSP), a controller, a microcontroller, a state machine, and the like. In some environments, "processor" may also refer to an application-specific integrated circuit (ASIC), a programmable logic device (PLD), a field programmable gate array (FPGA), or the like. For example, the term "processor" may also refer to a combination of processing devices such as a combination of a DSP and a microprocessor, a combination of a plurality of microprocessors, a combination of one or more microprocessors combined with a DSP core, or a combination of other arbitrary configurations.

The term "memory" should be interpreted in a wide sense to include an arbitrary electronic component that can store electronic information. The term "memory" may also refer to various types of processor-readable media such as a random access memory (RAM), a read-only memory (ROM), a nonvolatile random access memory (NVRAM), a programmable read-only memory (PROM), an erasable-programmable read-only memory (EPROM), an electrically erasable PROM (EEPROM), a flash memory, a magnetic or optical data storage device and registers. When a processor is able to read information from a memory and/or record information in the memory, the memory referred to as being in an electronic communication state with the processor. A memory integrated in a processor is in an electronic communication state with the processor.

Hereinafter, embodiments will be described in detail with reference to the accompanying drawings to allow those of ordinary skill in the art to which the present disclosure pertains to easily carry out the embodiments. Also, parts unrelated to the description are omitted from the drawings to clearly describe the present disclosure.

FIG. 1 is a view illustrating a movable radiographic imaging apparatus according to one embodiment of the present disclosure.

One example of a radiographic imaging apparatus 100 in the form of a C-arm according to an embodiment of the present disclosure is illustrated in FIG. 1. However, the present disclosure is not limited thereto, and the radiographic imaging apparatus 100 of the present disclosure may have various other forms.

For example, the radiographic imaging apparatus according to an embodiment of the present disclosure may be configured in the form of a C-arm as illustrated in FIG. 1 and obtain a moving image. The radiographic imaging apparatus may capture an image of a region of interest of a subject S, which is a target of which an image is to be captured, using radiation such as X-rays.

Referring to FIG. 1, the radiographic imaging apparatus 100 may have a radiation irradiator 111 outputting radiation, for example, X-rays, and an image obtainer 112 obtaining image data by receiving the radiation passing through the subject S, and the radiation irradiator 111 and the image obtainer 112 may be supported at both side ends of a C-arm 110. For example, the radiographic imaging apparatus may be applied to a mobile type C-arm X-ray imaging device, an interventional X-ray device, an interventional angiography C-arm X-ray device, and the like.

A support structure is configured to support the radiation irradiator 111 and the image obtainer 112 and enable the spatial positions and rotary positions of the radiation irradiator 111 and the image obtainer 112 to be changed to change an imaging position, an imaging angle, and the like of the subject S. For example, the support structure may include a support body 150, a lift column 130 fastened to the support body 150 to be movable in an up-down direction D1, and a forward-backward moving arm 120 fastened to the lift column 130 to be movable relative to the lift column 130 in a horizontal direction D2 while also movable in the up-down direction together with the lift column 130.

The C-arm 110 is fastened to the forward-backward moving arm 120 to be rotatable relative to the forward-backward moving arm 120 in at least one rotation direction, and the radiation irradiator 111 and the image obtainer 112 are respectively fastened to both side ends of the C-arm 110. Here, the C-arm 110 may be fastened to the forward-backward moving arm 120 to be movable relative to the forward-backward moving arm 120 in at least one rotation direction, for example, at least one rotation direction of an orbital rotation direction R1 and an axial rotation direction R2 about a direction parallel to the horizontal movement direction of the forward-backward moving arm 120, while being able to move upward or downward in the up-down direction and move forward or backward in the horizontal direction together with the forward-backward moving arm 120. Although not illustrated in the drawings, the support structure may include an actuator such as a motor for the movement of the lift column 130 in the up-down direction, the movement of the forward-backward moving arm 120 in the horizontal direction, and the rotation of the C-arm 110. Components for supporting and driving the C-arm 110 which is a support member supporting the radiation irradiator 111 and the image obtainer 112, that is, the forward-backward moving arm 120, the lift column 130, and actuators disposed therein, may be referred to as driving components for driving the C-arm 110, and a combination thereof may be referred to as a driver for driving the C-arm

110. Also, the C-arm 110 may be configured such that panning rotation is possible through horizontal rotation of the forward-backward moving arm 120. The shape of the support member is not limited to a C-shape, and an arm having a U-shape, a G-shape, an O-shape, or the like instead of a C-shape may also be used as the support member in another embodiment of the present disclosure.

A display 140 is configured to display at least one or more of real-time position information, image data, reference position information, and radiation output information. The display 140 may be any device that can display information and images, and for example, the display 140 may be a printer, a cathode ray tube (CRT) display, a liquid crystal display (LCD), a plasma display panel (PDP), an organic light emitting diode (OLED) display, a field emission display (FED), a light emitting diode (LED) display, a digital light processing (DLP) display, a flat panel display (FPD), a 3D display, a transparent display, or the like. Also, the display 140 may also be implemented in a form that enables display and input of information such as a touchscreen that can receive an input from a user.

Figure 2:
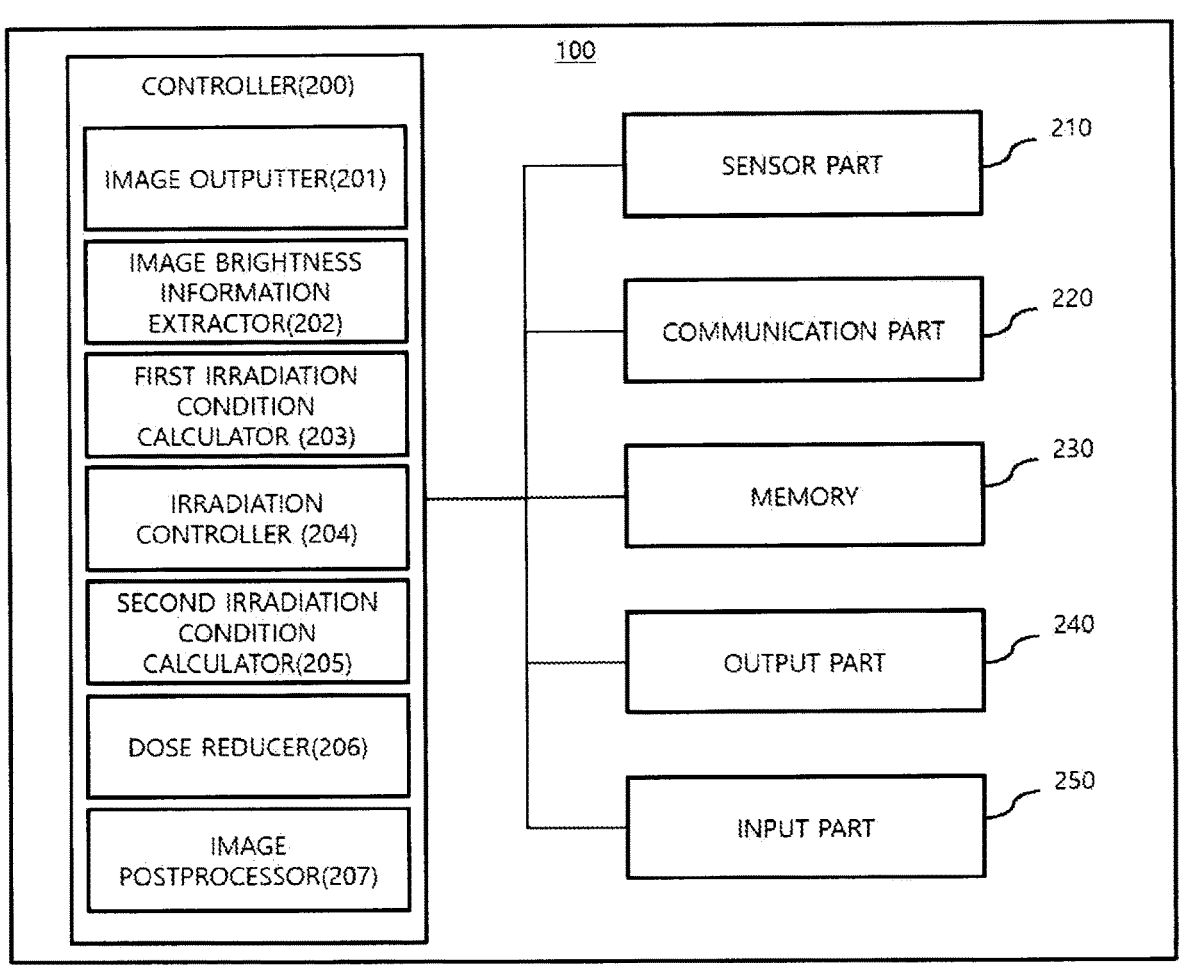
FIG. 2 is a view illustrating a block diagram of various components that may be included in the radiographic imaging apparatus according to one embodiment of the present disclosure.

FIG. 2 is a view illustrating a block diagram of various components that may be included in the radiographic imaging apparatus according to one embodiment of the present disclosure.

Referring to FIG. 2, the radiographic imaging apparatus 100 may include at least one of a controller 200, a sensor part 210, a communication part 220, a memory 230, an output part 240, and an input part 250. While FIG. 1 schematically shows an exterior of the radiographic imaging apparatus 100, FIG. 2 shows a block diagram by functionally dividing the radiographic imaging apparatus 100. At least one of the controller 200, the sensor part 210, the communication part 220, the memory 230, the output part 240, and the input part 250 of FIG. 2 may be included in at least one of the radiation irradiator 111, the image obtainer 112, the support body 150, the lift column 130, and the forward-backward moving arm 120 of FIG. 1 or may be coupled to an outer portion of at least one of the radiation irradiator 111, the image obtainer 112, the support body 150, the lift column 130, and the forward-backward moving arm 120.

The radiographic imaging apparatus 100 according to an embodiment of the present disclosure may include the controller 200. The controller 200 may be implemented in the form of an information processing device such as one or a plurality of computers capable of information processing and arithmetic operations. For example, a computer may include a control means such as a CPU, a storage means such as a ROM or a RAM, and a graphics control means such as a graphics processing unit (GPU). The computer may also include a communication means such as a network card and an input/output means such as a keyboard, a display, or a touchscreen. As known, such components of the computer may be connected through a bus and operated and controlled by execution of a program stored in the storage means.

The radiographic imaging apparatus 100 that may be implemented in the form of a computer capable of information processing may be configured to perform an image processing function by being installed at the radiographic imaging apparatus 100 illustrated in FIG. 1, and in this case, may be configured to, as part of the radiographic imaging apparatus, receive and process a captured image and allow the processed image to be displayed on the display 140 of the radiographic imaging apparatus.

The radiographic imaging apparatus 100 may include the sensor part 210. The sensor part 210 may obtain various pieces of information using at least one sensor. The sensor part 210 may be provided as a sensor using a measurement means such as a pressure measurement means, a potential measurement means, and an optical measurement means. For example, the sensor part 210 may include at least one of a distance measurement sensor or an encoder. Also, the sensor may include a pressure sensor, an infrared sensor, an LED sensor, a touch sensor, and the like. However, the present disclosure is not limited thereto. The sensor part may be included in at least one of the radiation irradiator 111, the image obtainer 112, the support body 150, the lift column 130, the forward-backward moving arm 120, and the C-arm 110.

Also, the radiographic imaging apparatus 100 may include the communication part 220. The communication part 220 may be a component allowing the radiographic imaging apparatus 100 to communicate with an internal module or an external device via a wire or wirelessly. The external device may be an external server or a user terminal. The user terminal may be a personal computer (PC), a smartphone, a tablet, or a wearable device. The communication part 220 may include a wired/wireless communication module for network connection. For example, wireless LAN (WLAN) (Wi-Fi), Wireless broadband (Wibro), World Interoperability for Microwave Access (Wimax), High Speed Downlink Packet Access (HSDPA), or the like may be used as wireless communication technology. For example, Digital Subscriber Line (XDSL), Fibers to the home (FTTH), Power Line Communication (PLC), or the like may be used as wired communication technology. Also, a network connector may include a short range communication module to transmit and receive data to and from any device/terminal located at a short distance. For example, Bluetooth, Radio Frequency Identification (RFID), Infrared Data Association (IrDA), Ultra-Wideband (UWB), ZigBee, or the like may be used as short range communication technology, but the present disclosure is not limited thereto.

The radiographic imaging apparatus 100 may include the memory 230. The controller 200 may execute instructions stored in the memory. The controller 200 and the memory 230 may be independent hardware, but the present disclosure is not limited thereto, and the controller 200 may include the memory 230. That is, the memory 230 may be included in the controller 200 or may be present outside the controller 200. The memory 230 may store various pieces of information related to the radiographic imaging apparatus 100. For example, the memory 230 may include information related to an operation method of the radiation irradiator 111 and include captured images and user authentication information, but the present disclosure is not limited thereto.

The memory 230 may be implemented using nonvolatile storage media that can continuously store arbitrary data. Examples of the memory 230 may include a storage device based on a flash memory and/or a battery backup memory as well as a disk, an optical disc, and a magneto-optical storage device, but the present disclosure is not limited thereto. The memory 230 may be a volatile storage device which is a main storage device directly accessed by a processor and in which stored information is instantaneously erased once the power is turned off, such as a random access memory (RAM) such as a dynamic random access memory (DRAM) or a static random access memory (SRAM), but the memory 230 is not limited thereto. The memory 230 may be operated by the controller 200. Also, the controller 200 may execute instructions included in the memory 230.

Also, the radiographic imaging apparatus 100 may further include a manipulation part providing an interface for manipulation of the radiographic imaging apparatus 100. The manipulation part may include the output part 240 and the input part 250.

The output part 240 may, under control of the controller 200, show imaging-related information such as irradiation of X-rays or output sound and images from which a state of a main body can be checked. The output part 240 may include the display 140. The output part 240 may include a speaker or a display. The output part 240 may output a medical image generated by the controller 200. The output part 240 may output information necessary for a user to manipulate the radiographic imaging apparatus 100, such as a user interface (UI), user information, or subject information. Examples of the output part 240 may include a speaker, a printer, a CRT display, an LCD, a PDP, an OLED display, an FED, an LED display, a vacuum fluorescent display (VFD), a DLP display, an FPD, a 3D display, a transparent display, and the like and may include various other output devices within the scope self-evident to those of ordinary skill in the art.

The radiographic imaging apparatus 100 may be connected to a workstation via a wire or wirelessly. The workstation may be present in a space physically separated from the radiographic imaging apparatus 100.

The workstation may include a storage server. The storage server may store medical images, information on a subject, information on a user (medical staff), and the like. The workstation may include a review device. The review device may receive a medical image from the storage server based on a command of the user and diagnose the medical image. The workstation and the radiographic imaging apparatus 100 may send, store, process, and output data according to the Digital Imaging and Communications in Medicine (DICOM) standard. Also, the workstation may include a Picture Archiving and Communication System (PACS).

The workstation may include an output part, an input part, and a controller. The output part and the input part provide an interface for manipulation of the workstation and the radiographic imaging apparatus 100 to the user. The controller of the workstation may control the workstation and the radiographic imaging apparatus 100.

The radiographic imaging apparatus 100 may be controlled through the workstation or may be controlled by the controller 200 included in the radiographic imaging apparatus 100. Therefore, the user may control the radiographic imaging apparatus 100 through the workstation or may control the radiographic imaging apparatus 100 through the manipulation part and the controller 200 included in the radiographic imaging apparatus 100. In other words, the user may remotely control the radiographic imaging apparatus 100 through the workstation or may directly control the radiographic imaging apparatus 100.

The controller of the workstation and the controller 200 of the radiographic imaging apparatus 100 may be separate, but the present disclosure is not limited thereto. The controller of the workstation and the controller 200 of the radiographic imaging apparatus 100 may be implemented as a single integrated controller, and the integrated controller may be included in only one of the workstation and the radiographic imaging apparatus 100. Hereinafter, the controller 200 may be the controller of the workstation and/or the controller of the radiographic imaging apparatus 100.

The output part and the input part of the workstation and the output part 240 and the input part 250 of the radiographic imaging apparatus 100 may each provide an interface for manipulation of the radiographic imaging apparatus 100 to the user. The workstation and the radiographic imaging apparatus 100 may each include an output part and an input part, but the present disclosure is not limited thereto. The output part or input part may also be implemented in only one of the workstation and the radiographic imaging apparatus 100.

Hereinafter, the input part 250 is the input part of the workstation and/or the input part of the radiographic imaging apparatus 100, and the output part 240 is the output part of the workstation and/or the output part of the radiographic imaging apparatus 100.

The input part 250 may receive a command for manipulation of the radiographic imaging apparatus 100 and various pieces of information related to X-ray imaging from the user. The controller 200 may control or manipulate the radiographic imaging apparatus 100 based on the information input through the input part 250. Examples of the input part 250 may include a joystick, a keyboard, a mouse, a touchscreen, an imaging button, an unlocking button, a voice recognizer, a fingerprint recognizer, an iris recognizer, a human motion recognizer, and the like and may include other input devices self-evident to those of ordinary skill in the art.

The user may input a command for X-ray irradiation through the input part 250, and a switch for such command input may be provided on the input part 250. The switch may be provided so that an irradiation command for X-ray irradiation is input when the switch is pressed at least once.

For example, the switch may have a structure in which, when the user presses the switch, a preparation command instructing preheating for X-ray irradiation is input, and when the switch is pressed deeper in that state, an irradiation command for actual X-ray irradiation is input. When the user manipulates the switch in this way, the controller 200 generates a signal, that is, a preparation signal, corresponding to the command input through manipulation of the switch and transmits the preparation signal to a high voltage generator generating a high voltage for X-ray generation. The high voltage generator may be included in the radiation irradiator 111.

The high voltage generator included in the radiation irradiator 111 receives the preparation signal transmitted from the controller 200 and starts preheating, and when preheating is completed, transmits a preparation complete signal to the controller 200. Also, for X-ray detection, the image obtainer 112 also needs preparation for X-ray detection, and the controller 200 transmits the preparation signal to the image obtainer 112 to allow the image obtainer 112 to prepare for detection of X-rays passing through the subject while the high voltage generator performs preheating. The image obtainer 112 prepares for detection of X-rays upon receiving the preparation signal, and when preparation for detection is complete, transmits a detection preparation complete signal to the controller 200.

When preheating of the high voltage generator included in the radiation irradiator 111 is complete, and preparation for X-ray detection of the image obtainer 112 is complete, the controller 200 transmits an irradiation signal to the high voltage generator, the high voltage generator generates a high voltage and applies the high voltage to an X-ray source included in the radiation irradiator 111, and the X-ray source radiates X-rays. The X-ray source may vary an X-ray irradiation dose according to at least one of a tube voltage, a tube current, and an X-ray pulse irradiation time controlled by the controller 200.

When transmitting the irradiation signal, the controller 200 may transmit a sound or light output signal to the output part 240 for predetermined sound or light to be output from the output part 240 to allow the subject or user to be aware of X-ray irradiation. Also, the output part 240 may output sound or light indicating imaging-related information other than X-ray irradiation. The output part 240 may be included in the manipulation part but is not limited thereto, and the output part 240 or a part of the output part 240 may be located at a place different from a place where the manipulation part is located. For example, the output part 240 or a part of the output part 240 may be located on a wall of an imaging room where X-ray imaging of a subject is performed.

The controller 200 controls the positions of the radiation irradiator 111 and the image obtainer 112, an imaging timing, an imaging condition, and the like according to imaging conditions set by the user.

Specifically, the controller 200 controls the high voltage generator and the image obtainer 112 according to a command input through the input part 250 to control an X-ray irradiation timing, an X-ray intensity, an X-ray irradiation region, and the like. Also, the controller 200 adjusts the position of the image obtainer 112 according to a predetermined imaging condition and controls an operation timing of the image obtainer 112.

Also, the controller 200 generates a medical image of a subject using image data received through the image obtainer 112. Specifically, the controller 200 may receive image data from the image obtainer 112, remove noise of the image data, and adjust a dynamic range and interleaving to generate the medical image of the subject.

The workstation may further include a communication part (not illustrated) that may be connected to a server, a medical device, a portable terminal, and the like through a network. The workstation may be one external device.

Hereinafter, the controller 200 according to one embodiment of the present disclosure will be described in more detail. The controller 200 may include at least one of a hardware module or a software module. Here, a module may be at least one of hardware or software divided into functional units. More specifically, the controller 200 of the radiographic imaging apparatus 100 may include at least one of an image outputter 201, an image brightness information extractor 202, a first irradiation condition calculator 203, an irradiation controller 204, a second irradiation condition calculator 205, and a dose reducer 206.

The image outputter 201 may be a component outputting a first radiographic image included in continuous radiographic images obtained by radiographic imaging of a subject. The image outputter 201 may be a component included in the controller 200 to generate continuous radiographic images by processing data obtained from the image obtainer 112. However, the present disclosure is not limited thereto, and the image outputter 201 may also be a component included in the output part 240 to display an image generated by the controller 200. For example, the continuous radiographic images may be referred to as at least one of X-ray video, X-ray motion imaging, or fluoroscopy.

The radiographic imaging apparatus 100 may obtain continuous radiographic images. That is, the radiographic imaging apparatus 100 may obtain a moving image. The continuous radiographic images may include a plurality of still radiographic images. In the present disclosure, still radiographic images may be referred to as frame images.

The first radiographic image may be included in the continuous radiographic images. The first radiographic image may include at least one frame image. The first radiographic image may be an image obtained by processing at least one frame image. The radiographic imaging apparatus 100 may store a predetermined irradiation condition. The predetermined irradiation condition may include at least one of a predetermined tube voltage, a predetermined tube current, and a predetermined X-ray pulse irradiation time. The predetermined irradiation condition may be stored in the radiographic imaging apparatus 100 and automatically selected upon imaging. The predetermined irradiation condition may also be selected by the user. The radiographic imaging apparatus 100 may control the radiation irradiator 111 based on the predetermined irradiation condition to irradiate a subject with radiation, and the image obtainer 112 may obtain the first radiographic image.

The first radiographic image may include an image of a subject. For the subject to be clearly shown in the radiographic image, it may be necessary to change irradiation conditions according to subject information. However, the first radiographic image uses a predetermined irradiation condition and thus may not be an image optimized according to the subject information. Here, the subject information may include at least one of a thickness of the subject, a type of the subject, a site of the subject, a material of the subject, and a density of the subject. Therefore, the radiographic imaging apparatus 100 may further include the following components to determine irradiation conditions optimized for the subject while implementing low-dose imaging.

The image brightness information extractor 202 may obtain brightness information from the first radiographic image. The image brightness information extractor 202 may be included in the controller 200.

A region of interest may be automatically extracted and not require intervention of a user. The image brightness information extractor 202 may obtain brightness information based on at least one statistical value among a maximum value, a minimum value, a mean value, a median value, standard deviation, and the like of pixels and at least one of a distribution graph (e.g., histogram) of pixel values, feature points extracted from an image, and positions of the feature points. A process in which the image brightness information extractor 202 obtains brightness information will be described later.

The first irradiation condition calculator 203 may determine a first irradiation condition based on the brightness information. The first irradiation condition calculator 203 may also be included in the controller 200. The first irradiation condition calculator 203 may be a component for controlling the brightness information of the first radiographic image to become similar to predetermined brightness information. The first irradiation condition may be information for controlling the radiation irradiator 111. The first irradiation condition may include at least one of a first tube voltage, a first tube current, and a first X-ray pulse irradiation time.

The first irradiation condition calculator 203 may determine a value of at least one of the first tube voltage, the first tube current, and the first X-ray pulse irradiation time of the radiation irradiator 111 based on the brightness information of the first radiographic image. For example, an X-ray irradiation dose may increase with an increase in at least one of the first tube voltage and the first tube current. The first X-ray pulse irradiation time is a value proportional to the time during which the X-ray source emits X-rays, and an X-ray irradiation dose may increase with an increase in the first X-ray pulse irradiation time. Also, the brightness information of the first radiographic image may be brighter with an increase in the irradiation dose. However, the present disclosure is not limited thereto, and the brightness information of the first radiographic image may be darker with an increase in the irradiation dose. The first irradiation condition calculator 203 may determine the first irradiation condition including at least one of the first tube voltage, the first tube current, and the first X-ray pulse irradiation time for the brightness information of the first radiographic image to become similar to predetermined brightness information. The first irradiation condition may be different from a predetermined irradiation condition. However, in a specific case, the first irradiation condition may be the same as the predetermined irradiation condition.

The irradiation controller 204 may control a radiation dose based on the first irradiation condition. The irradiation controller 204 may be included in the controller 200. The irradiation controller 204 may control an operation of the radiation irradiator 111 based on the first irradiation condition including at least one of the first tube voltage, the first tube current, and the first X-ray pulse irradiation time obtained from the first irradiation condition calculator 203.

The radiation irradiator 111 may irradiate the subject with radiation based on the first irradiation condition. The image obtainer 112 may obtain a second radiographic image based on the radiation based on at least one of the determined tube voltage, tube current, and X-ray pulse irradiation time. The second radiographic image may be a radiographic image generated after the first radiographic image. The second radiographic image may be included in the continuous radiographic images. The second radiographic image may include at least one frame image of a moving image.

Also, when the first radiographic image is an image based on the predetermined irradiation condition, the second radiographic image may be an image based on the first irradiation condition. Since the subject shown in the second radiographic image will be similar to the predetermined brightness information, the subject may be clearly shown in the second radiographic image. Therefore, the user may easily diagnose a patient based on the second radiographic image. However, the second radiographic image may not be based on the lowest dose. The radiographic imaging apparatus 100 may further perform the following process to maintain image quality while using the lowest dose.

The second irradiation condition calculator 205 may be included in the controller 200. The second irradiation condition calculator 205 may determine a second irradiation condition based on the second radiographic image generated based on the first irradiation condition when an imaging site of the subject is fixed. The second irradiation condition may be an irradiation condition for implementing the lowest dose while maintaining image quality. The second irradiation condition may be different from the first irradiation condition. However, in a specific case, the second irradiation condition may be the same as the first irradiation condition. The second irradiation condition may include at least one of a second tube voltage, a second tube current, and a second X-ray pulse irradiation time. The second irradiation condition may be a minimum irradiation condition for keeping image quality of the fixed imaging site similar to the image quality according to the first irradiation condition.

A value resulting from subtracting the radiation dose based on the second irradiation condition from the radiation dose based on the first irradiation condition may be less than or equal to 70% of the dose based on the first irradiation condition. That is, the radiation dose based on the second irradiation condition may be greater than or equal to 30% of the radiation dose based on the first irradiation condition. In this way, since the radiation dose based on the second irradiation condition is less than the radiation dose based on the first irradiation condition, the patient or the user may be exposed to a low dose of radiation. However, the radiographic imaging apparatus 100 of the present disclosure may, by providing images of the same quality, improve convenience for the user while maintaining health of the patient and the user.

The dose reducer 206 may reduce or maintain a radiation dose based on the second irradiation condition. The dose reducer 206 may be included in the controller 200. The dose reducer 206 may be independent from the irradiation controller 204. However, the present disclosure is not limited thereto, and the dose reducer 206 may be the same component as the irradiation controller 204.

The dose reducer 206 may control a radiation dose based on the second irradiation condition. The dose reducer 206 may control an operation of the radiation irradiator 111 based on the second irradiation condition including at least one of the second tube voltage, the second tube current, and the second X-ray pulse irradiation time obtained from the second irradiation condition calculator 205.

The radiation irradiator 111 may irradiate the subject with radiation based on the second irradiation condition. The image obtainer 112 may obtain a third radiographic image based on the radiation based on at least one of the determined second tube voltage, second tube current, and X-ray pulse irradiation time. The third radiographic image may be a radiographic image generated after the second radiographic image. The third radiographic image may be included in the continuous radiographic images. The third radiographic image may include at least one frame image of a moving image.

Also, when the second radiographic image is an image based on the first irradiation condition, the third radiographic image may be an image based on the second irradiation condition. The third radiographic image may maintain almost the same quality as the second radiographic image. That is, the sharpness and noise of the subject shown in the third radiographic image may almost be the same as the sharpness and noise of the subject shown in the second radiographic image. However, a dose of radiation with which the subject is irradiated to obtain the third radiographic image may be lower than or equal to the dose of radiation with which the subject is irradiated to obtain the second radiographic image.

When the dose is reduced by the dose reducer 206, the first irradiation condition calculator 203 may be deactivated. That is, the radiographic imaging apparatus 100 may not obtain the first irradiation condition using the first irradiation condition calculator 203. The radiographic imaging apparatus 100 may not match the subject of the continuous radiographic images to the predetermined brightness information. The radiographic imaging apparatus 100 may capture continuous radiographic images based on the second irradiation condition. The radiographic imaging apparatus 100 may capture the third radiographic image using the lowest dose based on the second irradiation condition. The condition for obtaining the second irradiation condition is that the subject should be fixed, and when the subject does not move, a high-quality radiographic image may be obtained even when the lowest dose is used. Therefore, side effects on the user and the patient due to radiation may be reduced.

Also, the radiographic imaging apparatus 100 may generate an improved current frame image by accumulating and averaging pixel values included in a current frame image included in the third radiographic image output using the dose reduced by the dose reducer 206 and a previous frame image included in the third radiographic image. In the present disclosure, the pixel values may be pixel values of pixels included in a display, and one of a plurality of pixels included in the image obtainer 112 may be a pixel value indicating a degree of excitation due to radiation. The pixel value may have a value that is 10 bits or greater and 16 bits or less.

As described above, the third radiographic image may include at least one frame image. The third radiographic image may include a current frame image 830 and previous frame images 820. The current frame image may be a frame image most recently obtained through the image obtainer 112. The previous frame images 820 may be at least one frame image obtained before the current frame image. The previous frame images 820 may include a just-before frame image 822, an (n−2) frame image 821, and the like. The just-before frame image may be a frame image right before the current frame image.

The radiographic imaging apparatus 100 may generate an improved current frame image by accumulating and averaging the current frame image and a predetermined number of previous frame images. The predetermined number may be greater than or equal to 1. The predetermined number may be the number of frames. The radiographic imaging apparatus 100 may accumulate and average a pixel value of one pixel of the current frame image and pixel values of previous frame images at positions corresponding to the one pixel of the current frame image. The radiographic imaging apparatus 100 may obtain pixel values included in the improved current frame image by accumulating and averaging pixel values of pixels corresponding to each other in the current frame image and previous frame images. The pixels corresponding to each other means that a position (coordinate value) of a pixel in the current frame image and a position (coordinate value) of a pixel in a previous frame image are the same as each other. The radiographic imaging apparatus 100 may generate the improved current frame image by obtaining a cumulative mean value of all the pixels included in the current frame image and all the pixels included in the previous frame images.

As described above, since the subject does not move, changes in pixel values of pixels at the same position in the continuous frame images may be small. Therefore, when the improved current frame image is obtained by accumulating and averaging as above, an influence due to noise may be minimized. This is because noise is generated as pixel values of pixels change significantly.

The radiographic imaging apparatus 100 may further include an image postprocessor 207 postprocessing the third radiographic image output with the dose reduced by the dose reducer 206. The image postprocessor 207 may adjust at least one of brightness information and contrast information of at least one of the first radiographic image, the second radiographic image, and the third radiographic image to maintain predetermined brightness based on the predetermined brightness information. The image postprocessor 207 may process a radiographic image in terms of software instead of determining an irradiation condition for controlling the radiation irradiator 111 like the first irradiation condition calculator 203.

The image postprocessor 207 of the radiographic imaging apparatus 100 may adjust pixel values of the third radiographic image for the brightness information of the third radiographic image to be similar to the predetermined brightness information. The radiographic imaging apparatus 100 may adjust all the pixel values included in the third radiographic image using the same ratio or the same subtraction value, and the brightness information of the third radiographic image may become similar to the predetermined brightness information. The predetermined brightness information may be brightness information stored in the memory.

However, the present disclosure is not limited thereto, and the predetermined brightness information may be a value measured by the image brightness information extractor 202. For example, the radiographic imaging apparatus 100 may measure brightness information of at least one of the first radiographic image and the second radiographic image using the image brightness information extractor 202. The radiographic imaging apparatus 100 may measure brightness information of the second radiographic image. The image postprocessor 207 of the radiographic imaging apparatus 100 may adjust pixel values of the third radiographic image for the brightness information of the third radiographic image to be similar to the brightness information of the second radiographic image. The image postprocessor 207 may adjust at least one of the brightness information and the contrast information of the third radiographic image to be similar to at least one of the brightness information and the contrast information of the second radiographic image. The radiographic imaging apparatus 100 may adjust all the pixel values included in the third radiographic image using the same ratio or the same subtraction value, and the brightness information of the third radiographic image may become similar to the brightness information of the second radiographic image.

For reference, in the present disclosure, being similar may mean that a difference between two pieces of information is less than or equal to a predetermined range. For example, the brightness information of the second radiographic image being similar to the brightness information of the third radiographic image may mean that an absolute value of a difference between the brightness information of the second radiographic image and the brightness information of the third radiographic image is less than or equal to a predetermined range. The predetermined range may be a value greater than or equal to 0.

Hereinafter, an operation method of the radiographic imaging apparatus will be described in detail.

FIG. 3 is a flowchart illustrating an operation method of the radiographic imaging apparatus according to one embodiment of the present disclosure.

As described above, the radiographic imaging apparatus 100 may include the radiation irradiator 111 irradiating a subject with radiation. Also, the radiographic imaging apparatus 100 may include the image obtainer 112 generating continuous radiographic images by receiving the radiation radiated from the radiation irradiator 111 and passing through the subject.

The radiographic imaging apparatus 100 may include the controller 200 controlling the radiation irradiator 111 and the image obtainer 112. The controller 200 may perform the following operations.

The controller 200 may perform obtaining a first radiographic image (310). The image outputter 201 may output the first radiographic image. The first radiographic image may be included in the continuous radiographic images. The first radiographic image may include at least one frame image. The first radiographic image may be an image obtained by processing at least one frame image. The radiographic imaging apparatus 100 may store a predetermined irradiation condition. The predetermined irradiation condition may include at least one of a predetermined tube voltage, a predetermined tube current, and a predetermined X-ray pulse irradiation time. The radiographic imaging apparatus 100 may control the radiation irradiator 111 based on the predetermined irradiation condition to irradiate the subject with radiation. The image obtainer 112 may obtain the first radiographic image.

The controller 200 may perform obtaining brightness information based on the first radiographic image included in the continuous radiographic images (320). The brightness information may be obtained by the image brightness information extractor 202.

The controller 200 may perform determining a first irradiation condition based on the brightness information according to a first algorithm (330). As described above, the first irradiation condition may be determined by the first irradiation condition calculator 203.

Step (320) and Step (330) will be described in more detail with reference to FIG. 4.

Figure 4:
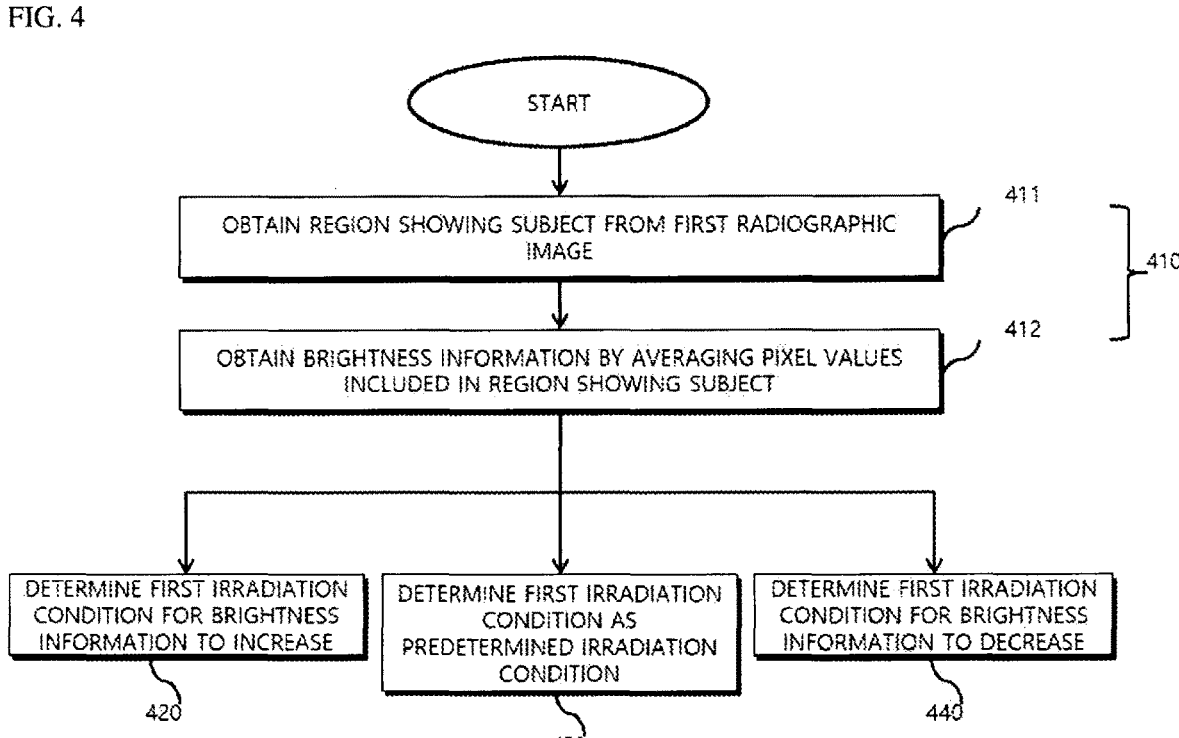
FIG. 4 is a flowchart illustrating the operation method of the radiographic imaging apparatus according to one embodiment of the present disclosure.

FIG. 4 is a flowchart illustrating the operation method of the radiographic imaging apparatus according to one embodiment of the present disclosure.

The obtaining of the brightness information (320) may include the following steps.

The controller 200 may perform obtaining brightness information by averaging pixel values included in at least a part of the first radiographic image (410). In order to obtain the brightness information by averaging the pixel values included in at least a part of the first radiographic image, the controller 200 may perform obtaining a region showing the subject from the first radiographic image based on a subject region obtaining model (411). The controller 200 may determine the region showing the subject from the first radiographic image based on a predetermined algorithm. The predetermined algorithm may be a machine learning model and a rule base model. The controller 200 may determine the region showing the subject based on subject information and the first radiographic image. Here, the subject information may include at least one of a thickness of the subject, a type of the subject, a site of the subject, a material of the subject, and a density of the subject. The predetermined algorithm may be selected based on the subject information. The controller 200 may determine the region showing the subject in the first radiographic image based on the selected predetermined algorithm. The region showing the subject may be a partial region of the first radiographic image. The region showing the subject may indicate an internal region of a contour of the subject shown in the first radiographic image.

The controller 200 may perform obtaining brightness information by averaging pixel values included in the region showing the subject (412). However, the present disclosure is not limited thereto, and the controller 200 may obtain at least one of a minimum value, a mean value, and a median value of pixel values of pixels of the region showing the subject as brightness information. However, the present disclosure is not limited thereto, and the controller 200 may obtain at least one of a minimum value, a mean value, and a median value of pixel values of all the pixels of the first radiographic image as brightness information.

The controller 200 may perform the following process to perform the determining of the first irradiation condition (330).

The controller 200 may perform determining the first irradiation condition for the brightness information to increase when the brightness information is less than predetermined first threshold brightness information (420). Also, the controller 200 may perform determining the first irradiation condition for the brightness information to decrease when the brightness information is greater than the predetermined first threshold brightness information (440).

Also, the controller 200 may perform determining the first irradiation condition as the predetermined irradiation condition when the brightness information is the same as the predetermined first threshold brightness information (430). The predetermined irradiation condition may be an irradiation condition used to obtain the first radiographic image.

As described above, the first irradiation condition may include at least one of the first tube voltage, the first tube current, and the first X-ray pulse irradiation time. The first irradiation condition calculator 203 may determine a value of at least one of the first tube voltage, the first tube current, and the first X-ray pulse irradiation time of the radiation irradiator 111 based on the brightness information of the first radiographic image. For example, an X-ray irradiation dose may increase with an increase in at least one of the first tube voltage and the first tube current. The first X-ray pulse irradiation time is a value proportional to the time during which the X-ray source emits X-rays, and an X-ray irradiation dose may increase with an increase in the first X-ray pulse irradiation time. At least one of the first tube voltage, the first tube current, and the first X-ray pulse irradiation time may have a linear relationship with the irradiation dose. However, the present disclosure is not limited thereto, and at least one of the first tube voltage, the first tube current, and the first X-ray pulse irradiation time may have a nonlinear relationship with the irradiation dose.

The controller 200 may determine at least one of the first tube voltage, the first tube current, and the first X-ray pulse irradiation time included in the first irradiation condition by modifying at least one of the predetermined tube voltage, the predetermined tube current, and the predetermined X-ray pulse irradiation time included in the predetermined irradiation condition based on at least one of a predetermined first irradiation condition function and a predetermined first irradiation condition table. The first irradiation condition function or first irradiation condition table may be a function or table for determining the first irradiation condition according to the predetermined irradiation condition and the brightness information of the first radiographic image.

According to one embodiment of the present disclosure, the brightness information of the first radiographic image may be brighter with an increase in the irradiation dose. Here, when the brightness information is less than the predetermined first threshold brightness information, the first irradiation condition may be greater than the predetermined irradiation condition. That is, when the brightness information is less than the predetermined first threshold brightness information, at least one of the first tube voltage, the first tube current, and the first X-ray pulse irradiation time included in the first irradiation condition may be greater than at least one of the predetermined tube voltage, the predetermined tube current, and the predetermined X-ray pulse irradiation time included in the predetermined irradiation condition. Also, when the brightness information is greater than the predetermined first threshold brightness information, the first irradiation condition may be less than the predetermined irradiation condition. That is, when the brightness information is greater than the predetermined first threshold brightness information, at least one of the first tube voltage, the first tube current, and the first X-ray pulse irradiation time included in the first irradiation condition may be less than at least one of the predetermined tube voltage, the predetermined tube current, and the predetermined X-ray pulse irradiation time included in the predetermined irradiation condition. Also, when the brightness information is the same as the predetermined first threshold brightness information, the first irradiation condition may be the same as the predetermined irradiation condition. That is, when the brightness information is the same as the predetermined first threshold brightness information, at least one of the first tube voltage, the first tube current, and the first X-ray pulse irradiation time included in the first irradiation condition may be the same as at least one of the predetermined tube voltage, the predetermined tube current, and the predetermined X-ray pulse irradiation time included in the predetermined irradiation condition.

However, the present disclosure is not limited thereto, and according to various embodiments of the present disclosure, the brightness information of the first radiographic image may be darker with an increase in the irradiation dose. For example, the controller 200 may use an inverted image obtained by inverting pixel values of an image obtained from the image obtainer 112. Therefore, the brightness information of the first radiographic image, which is an inverted image, may be darker with an increase in the irradiation dose. Here, when the brightness information is less than the predetermined first threshold brightness information, the first irradiation condition may be less than the predetermined irradiation condition. That is, when the brightness information is less than the predetermined first threshold brightness information, at least one of the first tube voltage, the first tube current, and the first X-ray pulse irradiation time included in the first irradiation condition may be less than at least one of the predetermined tube voltage, the predetermined tube current, and the predetermined X-ray pulse irradiation time included in the predetermined irradiation condition. Also, when the brightness information is greater than the predetermined first threshold brightness information, the first irradiation condition may be greater than the predetermined irradiation condition. That is, when the brightness information is greater than the predetermined first threshold brightness information, at least one of the first tube voltage, the first tube current, and the first X-ray pulse irradiation time included in the first irradiation condition may be greater than at least one of the predetermined tube voltage, the predetermined tube current, and the predetermined X-ray pulse irradiation time included in the predetermined irradiation condition.

In this way, the controller 200 may determine the first irradiation condition including at least one of the first tube voltage, the first tube current, and the first X-ray pulse irradiation time for the brightness information of the first radiographic image to become equal to the predetermined brightness information. The first irradiation condition may be different from the predetermined irradiation condition. However, in a specific case, the first irradiation condition may be the same as the predetermined irradiation condition. The controller 200 may cause the brightness information of the radiographic image generated after the first radiographic image to be equal to the predetermined brightness information based on the first irradiation condition.

The controller 200 may repeatedly obtain the first irradiation condition in a predetermined cycle. The radiographic imaging apparatus 100 may provide a moving image, and the subject may change continuously. The radiographic imaging apparatus 100 may provide an optimized radiographic image to the user by continuously obtaining the first irradiation condition and radiating radiation according thereto.

Referring back to FIG. 3, the controller 200 may perform controlling a radiation dose based on the first irradiation condition (340). Step (340) may be performed by the irradiation controller 204. As described above, the radiation dose may be determined from at least one of the first tube voltage, the first tube current, and the first X-ray pulse irradiation time included in the first irradiation condition.

The controller 200 may perform obtaining a second radiographic image included in the continuous radiographic images and generated based on the first irradiation condition (350). The second radiographic image may be a radiographic image generated after the first radiographic image. The second radiographic image may be included in the continuous radiographic images. The second radiographic image may include at least one frame image of a moving image. Also, when the first radiographic image is an image based on the predetermined irradiation condition, the second radiographic image may be an image based on the first irradiation condition. Since the subject shown in the second radiographic image will be similar to the predetermined brightness information, the subject may be clearly shown in the second radiographic image. Therefore, the user may easily diagnose a patient based on the second radiographic image. However, the second radiographic image may not be based on the lowest dose. The radiographic imaging apparatus 100 may further perform the following process to maintain image quality while using the lowest dose.

The controller 200 may perform obtaining movement presence/absence information indicating whether an imaging site of the subject is fixed (360). The movement presence/absence information may be obtained from the user through the input part 250. For example, the user may input movement presence/absence information to the radiographic imaging apparatus 100 after checking that the subject is staying still.

However, the present disclosure is not limited thereto, and the movement presence/absence information may also be obtained automatically. More specifically, the obtaining of the movement presence/absence information (360) may include the following process.

The controller 200 may perform determining the movement presence/absence information to indicate that the imaging site of the subject is not fixed when less than a predetermined threshold amount of time has passed from a time at which at least one of the first radiographic image and the second radiographic image was obtained. The threshold amount of time may be an amount of time sufficient for the patient to be fixed. In a main environment, the subject may be a patient who is a target of surgery. The patient may be in an anesthetic state for surgery. When the patient is placed on the radiographic imaging apparatus, the patient may hardly move. Therefore, in the radiographic imaging apparatus 100, the controller 200 may determine the movement presence/absence information to indicate that the imaging site of the subject is not fixed when less than the predetermined threshold amount of time has passed from a time at which at least one of the first radiographic image and the second radiographic image began to be obtained. Here, the time at which the first radiographic image begins to be obtained may be a time at which an initial radiographic image of the subject begins to be obtained. Also, the time at which the second radiographic image begins to be obtained may be a time at which a radiographic image begins to be obtained according to the first irradiation condition. The time at which the second radiographic image begins to be obtained may also be a time at which obtaining of the first radiographic image ends. A difference between the time at which the first radiographic image begins to be obtained and the time at which the second radiographic image begins to be obtained may be within 5 seconds.

The controller may perform determining the movement presence/absence information to indicate that the imaging site of the subject is fixed when the predetermined threshold amount of time or more has passed from the time at which at least one of the first radiographic image and the second radiographic image was obtained. That is, the radiographic imaging apparatus 100 may assume that the subject is fixed after the predetermined threshold amount of time.

The controller 200 may perform determining a second irradiation condition based on the second radiographic image according to a second algorithm when the movement presence/absence information indicates that the imaging site of the subject is fixed (370). Step (370) may be performed by the second irradiation condition calculator 205.

The first algorithm for determining the first irradiation condition and the second algorithm for determining the second irradiation condition may be different from each other. Hereinafter, the determining of the second irradiation condition (370) will be described with reference to FIG. 5.

Figure 5:
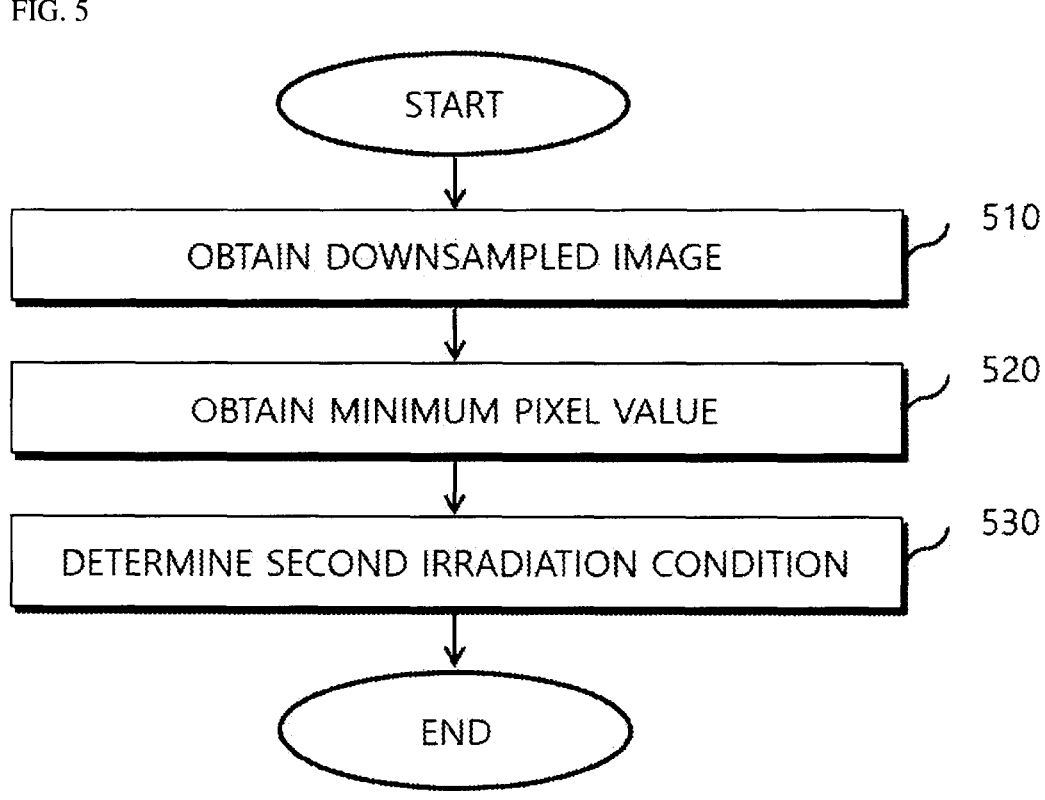
FIG. 5 is a flowchart illustrating an operation of the radiographic imaging apparatus according to one embodiment of the present disclosure.

FIG. 5 is a flowchart illustrating an operation of the radiographic imaging apparatus according to one embodiment of the present disclosure. Also, FIG. 6 is a view for describing downsampling according to one embodiment of the present disclosure.

Figure 6:
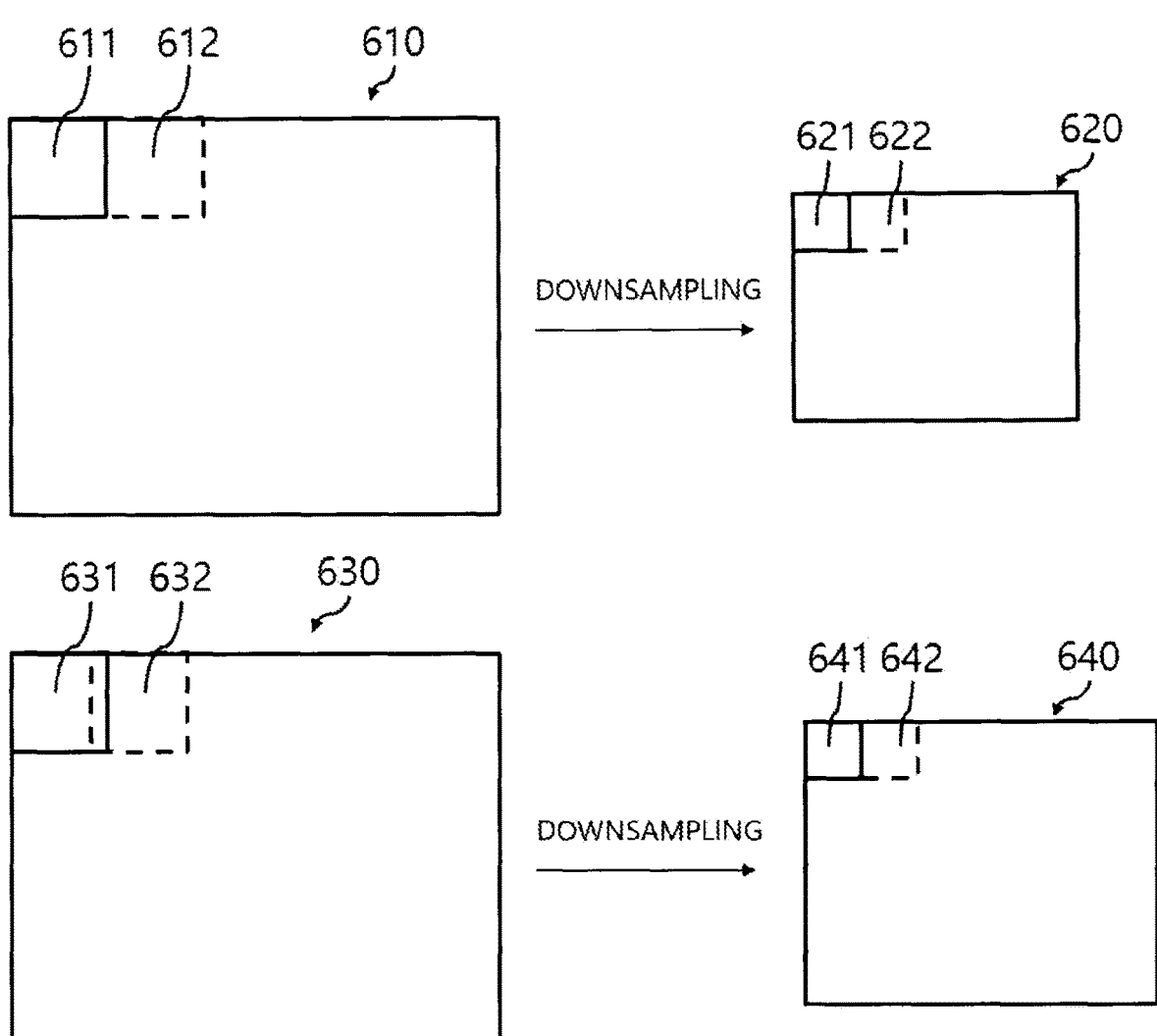
FIG. 6 is a view for describing downsampling according to one embodiment of the present disclosure.

Referring to FIGS. 5 and 6, the determining of the second irradiation condition (370) may include the following operation. The controller 200 may perform obtaining a downsampled image 620 by downsampling a second radiographic image 610 into units of patches 611 of a predetermined size. The patch 611 of the predetermined size may be smaller than the second radiographic image 610. When the size of the second radiographic image 610 is n×m, the size of the patch 611 of the predetermined size may be a×b. n may be the number of pixels along the horizontal axis included in the second radiographic image 610, and m may be the number of pixels along the vertical axis included in the second radiographic image 610. Also, a may be the number of pixels along the horizontal axis of the patch 611 of the predetermined size, and b may be the number of pixels along the vertical axis of the patch 611 of the predetermined size. n may be greater than or equal to a, and m may be greater than or equal to b.

The controller 200 may determine one of a mean value, a minimum value, a maximum value, and a median value of pixel values of pixels included in the patch 611 of the predetermined size in the second radiographic image 610 as a pixel value of one pixel 621 of the downsampled image 620. The controller 200 may determine one of a mean value, a minimum value, a maximum value, and a median value of pixel values of pixels included in the next patch 612 of the predetermined size in the second radiographic image 610 as a pixel value of one pixel 622 of the downsampled image 620. The sizes of the patch 611 of the predetermined size and the next patch 612 of the predetermined size may be the same, and the patch 611 and the next patch 612 may not overlap each other. The controller 200 may obtain the downsampled image 620 by repeating the above process for the entire second radiographic image 610.

Although the patches 611 and 612 of the predetermined size are described above as not overlapping each other, the present disclosure is not limited thereto. The patches of the predetermined size may overlap each other. For example, the controller 200 may determine one of a mean value, a minimum value, a maximum value, and a median value of pixel values of pixels included in a patch 631 of a predetermined size in a second radiographic image 630 as a pixel value of one pixel 641 of a downsampled image 640. The controller 200 may determine one of a mean value, a minimum value, a maximum value, and a median value of pixel values of pixels included in the next patch 632 of a predetermined size in the second radiographic image 630 as a pixel value of one pixel 642 of the downsampled image 640. The sizes of the patch 631 of the predetermined size and the next patch 632 of the predetermined size may be the same, and the patch 631 and the next patch 632 may overlap each other. The controller 200 may obtain the downsampled image 640 by repeating the above process for the entire second radiographic image 630. When downsampling is performed with the patches of the predetermined size overlapping each other, the downsampled image 640 may be larger than the downsampled image 620.

Although downsampling is described above as being performed for the entire region of the second radiographic image 630, the present disclosure is not limited thereto. The controller 200 may obtain a downsampled image by performing downsampling for a region of interest in the second radiographic image. The region of interest may be a region selected by the user or a region automatically selected by the radiographic imaging apparatus 100. For example, the region of interest may be a region showing the subject. Since the region showing the subject has been described above, overlapping description thereof will be omitted.

The controller 200 may perform obtaining a minimum pixel value among pixel values included in the downsampled image (one of 620 and 640). The controller 200 may perform determining the second irradiation condition for the minimum pixel value to become equal to predetermined second threshold brightness information when the minimum pixel value is greater than the second threshold brightness information. The controller 200 may perform determining the second irradiation condition to be the same as the first irradiation condition when the minimum pixel value is less than or equal to the predetermined second threshold brightness information. The controller 200 may not determine the second irradiation condition when the minimum pixel value is less than or equal to the predetermined second threshold brightness information. The second threshold brightness information may be obtained based on performance of a detector. The second threshold brightness information is the smallest pixel value that can be processed without a problem in at least one of the image obtainer 112 and the image postprocessor 207 included in the controller 200, and may be a predefined constant. A noise component may be present in a pixel when performance of the image obtainer 112 and the image postprocessor 207 is not good, and a value less than or equal to a specific pixel value may be a value due to noise instead of a value due to radiation. Therefore, the second threshold brightness information may be a value related to a minimum radiation dose that may indicate that pixels are excited due to radiation. That is, the second threshold brightness information may decrease with better performance of the image obtainer 112 and the image postprocessor 207.

The determining of the second irradiation condition for the minimum pixel value to become equal to the second threshold brightness information will be described with reference to FIG. 7.

Figure 7:
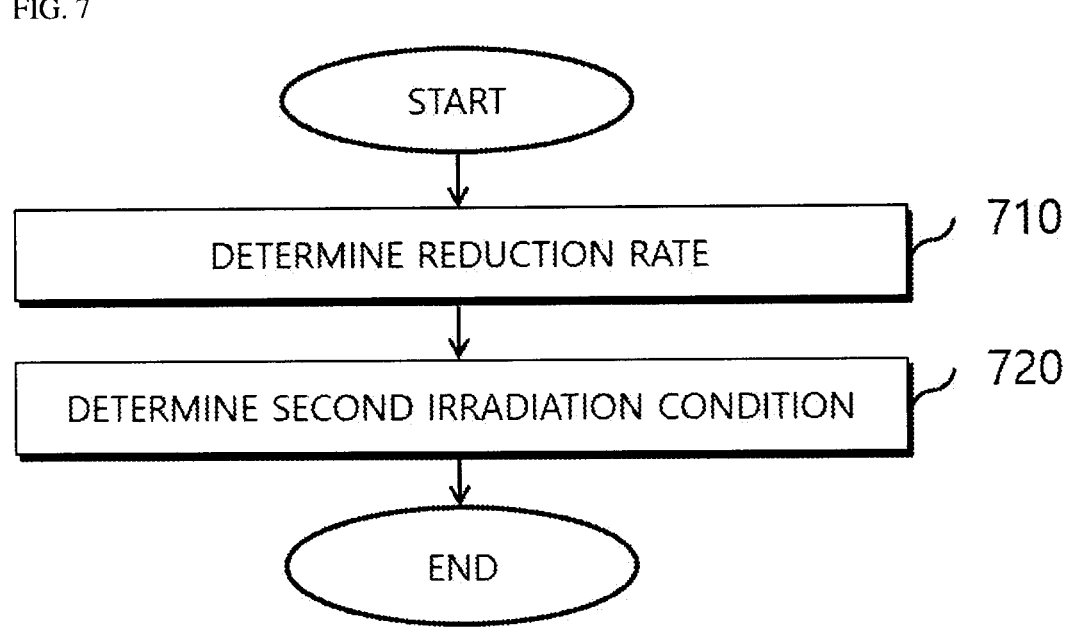
FIG. 7 is a flowchart for describing a process for obtaining a second irradiation condition according to one embodiment of the present disclosure.

FIG. 7 is a flowchart for describing a process for obtaining the second irradiation condition according to one embodiment of the present disclosure.

The determining of the second irradiation condition for the minimum pixel value to become equal to the second threshold brightness information may include the following process.

The controller 200 may perform determining a reduction rate based on the minimum pixel value and the second threshold brightness information (710). The second threshold brightness information is the smallest pixel value that can be processed without a problem in at least one of the image obtainer 112 and the image postprocessor 207 included in the controller 200, and may be a predefined constant. The reduction rate may be greater than or equal to 0 and less than or equal to a predetermined maximum reduction rate. The maximum reduction rate may be 65% or more and 75% or less. For example, the maximum reduction rate may be 70%. The unit of the reduction rate may be percentage. However, the present disclosure is not limited thereto.

The controller 200 may obtain the reduction rate based on the following equation.

$$\text{Reduction rate} = \min(\max(1 - \text{second threshold brightness information} / \text{minimum pixel value}, 0), \text{maximum reduction rate}) \times 100$$

The radiation dose based on the second irradiation condition may be greater than or equal to 30% of the radiation dose based on the first irradiation condition. When the reduction rate is determined as 70% which is the maximum reduction rate, the radiation dose based on the second irradiation condition may be 30% of the radiation dose based on the first irradiation condition.

The controller 200 may perform determining the second irradiation condition for the radiation irradiator to radiate radiation with a dose resulting from subtracting a value obtained by multiplying the dose based on the first irradiation condition by the reduction rate from the dose based on the first irradiation condition (720).

The second irradiation condition may include at least one of the second tube voltage, the second tube current, and the second X-ray pulse irradiation time. The controller 200 may determine a value of at least one of the second tube voltage, the second tube current, and the second X-ray pulse irradiation time based on the reduction rate determined in step (710). For example, an X-ray irradiation dose may increase with an increase in at least one of the second tube voltage and the second tube current. The second X-ray pulse irradiation time is a value proportional to the time during which the X-ray source emits X-rays, and an X-ray irradiation dose may increase with an increase in the second X-ray pulse irradiation time. Also, brightness information of a radiographic image may be brighter with an increase in the irradiation dose. However, the present disclosure is not limited thereto, and brightness information of a radiographic image may be darker with an increase in the irradiation dose. The controller 200 may determine the second irradiation condition including at least one of the second tube voltage, the second tube current, and the second X-ray pulse irradiation time according to the reduction rate. The second irradiation condition may be different from the first irradiation condition. However, in a specific case, the second irradiation condition may also be the same as the first irradiation condition.

At least one of the second tube current and the second X-ray pulse irradiation time may have a linear relationship with the irradiation dose. Also, the second tube voltage may have a nonlinear relationship with the irradiation dose. The controller 200 may determine at least one of the second tube current and the second X-ray pulse irradiation time by reducing at least one of the first tube current and the first X-ray pulse irradiation time by the reduction rate. However, the present disclosure is not limited thereto, and the controller 200 may determine at least one of the second tube current and the second X-ray pulse irradiation time corresponding to the reduction rate by applying at least one of the first tube current and the first X-ray pulse irradiation time to a predetermined reduction rate determination function or a predetermined reduction rate determination table. Also, the controller 200 may obtain a voltage reduction rate corresponding to the reduction rate based on a voltage reduction rate determination function or a voltage reduction rate determination table. The controller 200 may determine the second tube voltage by reducing the first tube voltage by the voltage reduction rate.

Referring back to FIG. 3, the controller 200 may perform controlling the radiation dose based on the second irradiation condition (380). Step (380) may be performed by at least one of the dose reducer 206 and the irradiation controller 204. As described above, the second irradiation condition may be determined based on the first irradiation condition and the reduction rate. The radiation dose based on the second irradiation condition may be less than or equal to the radiation dose based on the first irradiation condition. That is, the dose according to the second irradiation condition may be determined using the following equation according to the second irradiation condition by the controller 200.

$$\text{Dose according to second irradiation condition=dose} \\ \text{according to first irradiation condition} \times (1-\text{re-} \\ \text{duction rate}/100)$$

The controller 200 may perform obtaining a third radiographic image included in the continuous radiographic images and generated based on the second irradiation condition (390). The third radiographic image may be a radiographic image generated after the second radiographic image. The third radiographic image may be included in the continuous radiographic images. The third radiographic image may include at least one frame image of a moving image.

Also, when the second radiographic image is an image based on the first irradiation condition, the third radiographic image may be an image based on the second irradiation condition. The third radiographic image may maintain almost the same quality as the second radiographic image. That is, the sharpness and noise of the subject shown in the third radiographic image may almost be the same as the sharpness and noise of the subject shown in the second radiographic image. However, a dose of radiation with which the subject is irradiated to obtain the third radiographic image may be lower than or equal to the dose of radiation with which the subject is irradiated to obtain the second radiographic image.

The controller 200 may repeatedly obtain the second irradiation condition in a predetermined cycle. The radiographic imaging apparatus 100 may provide a moving image, and the subject may change continuously. The radiographic imaging apparatus 100 may obtain radiographic images of the subject with a low dose and maintain high quality of the radiographic images by continuously obtaining the second irradiation condition and radiating radiation according thereto.

According to the radiographic imaging apparatus 100 according to one embodiment of the present disclosure, the controller 200 may fix the second irradiation condition based on a user input or a predetermined condition. When the controller 200 fixes the second irradiation condition, since the second irradiation condition is not changed when an object other than the subject additionally enters an imaging region, an effect of maintaining a low dose may be expected. For example, when a medical device or the like enters the imaging region, the radiographic imaging apparatus 100 may maintain a low dose according to the second irradiation condition instead of changing an irradiation dose of radiation to change the brightness of the radiographic image.

The third radiographic image may be postprocessed to improve image quality. Hereinafter, a process in which the third radiographic image is postprocessed will be described.

Figure 8:
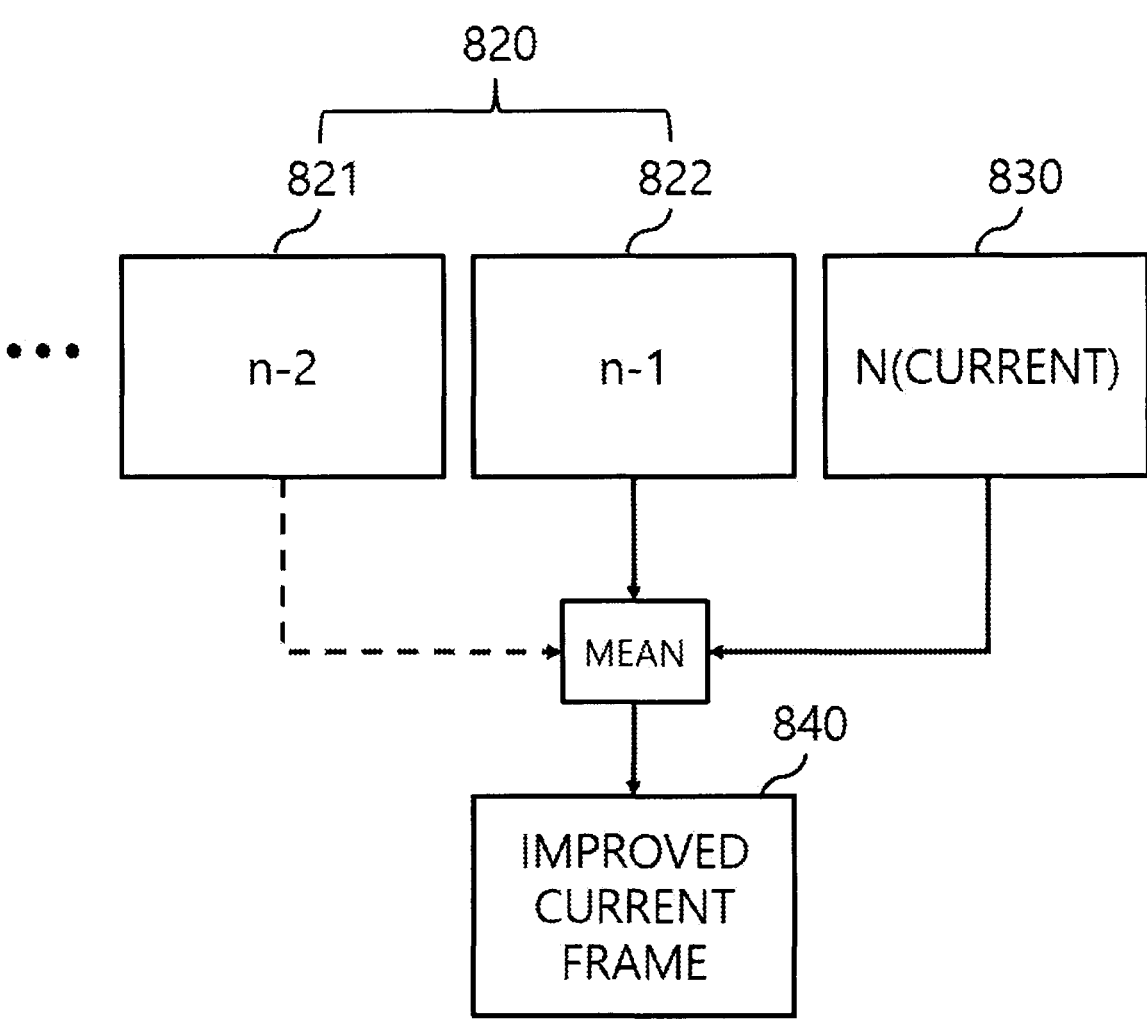
FIG. 8 is a view for describing an operation of the radiographic imaging apparatus according to one embodiment of the present disclosure.

FIG. 8 is a view for describing an operation of the radiographic imaging apparatus according to one embodiment of the present disclosure.

The obtaining of the third radiographic image (390) may include the following process. The controller 200 may perform generating an improved current frame image 840 by accumulating and averaging pixel values included in at least a part of a current frame image 830 included in the third radiographic image and pixel values included in at least a part of previous frame images 820 included in the third radiographic image. The obtaining of the improved current frame image 840 may be performed by the image postprocessor 207 included in the controller 200.

As described above, the third radiographic image may include the current frame image 830 and the previous frame images 820. The current frame image may be a frame image most recently obtained through the image obtainer 112. The previous frame images 820 may be at least one frame image obtained before the current frame image. The previous frame images 820 may include a just-before frame image 822 and an (n−2) frame image 821. The just-before frame image may be a frame image right before the current frame image.

The controller 200 may generate the improved current frame image 840 by accumulating and averaging the current frame image 830 and a predetermined number of previous frame images 820. The predetermined number may be greater than or equal to 1. The predetermined number may be the number of frames. Hereinafter, for convenience of description, the case in which the predetermined number is 1 will be described. The same description may apply for the case in which the predetermined number is 2 or greater.

The controller 200 may accumulate and average a pixel value of one pixel of the current frame image 830 and a pixel value of the previous frame image 820 at a position corresponding to the one pixel of the current frame image. The radiographic imaging apparatus 100 may obtain pixel values included in the improved current frame image 840 by accumulating and averaging pixel values of pixels corresponding to each other in the current frame image 830 and previous frame image 820. The pixels corresponding to each other means that a position (coordinate value) of a pixel in the current frame image 830 and a position (coordinate value) of a pixel in the previous frame image 820 are the same as each other. The controller 200 may generate the improved current frame image 840 by obtaining a cumulative mean value of all the pixels included in the current frame image 830 and all the pixels included in the previous frame image 820. However, the present disclosure is not limited thereto, and the controller 200 may generate the improved current frame image 840 by obtaining a cumulative mean value of pixel values of pixels included in at least a part of the current frame image 830 and pixel values of pixels included in at least a part of the previous frame image 820. At least a part of the current frame image 830 may be at least one of a region of interest or a region showing the subject.

As described above, since the subject does not move, changes in pixel values of pixels at the same position in the continuous frame images may be small. Therefore, when the improved current frame image is obtained by accumulating and averaging as above, an influence due to noise may be minimized. This is because noise is generated as pixel values of pixels change significantly.

Figure 9:
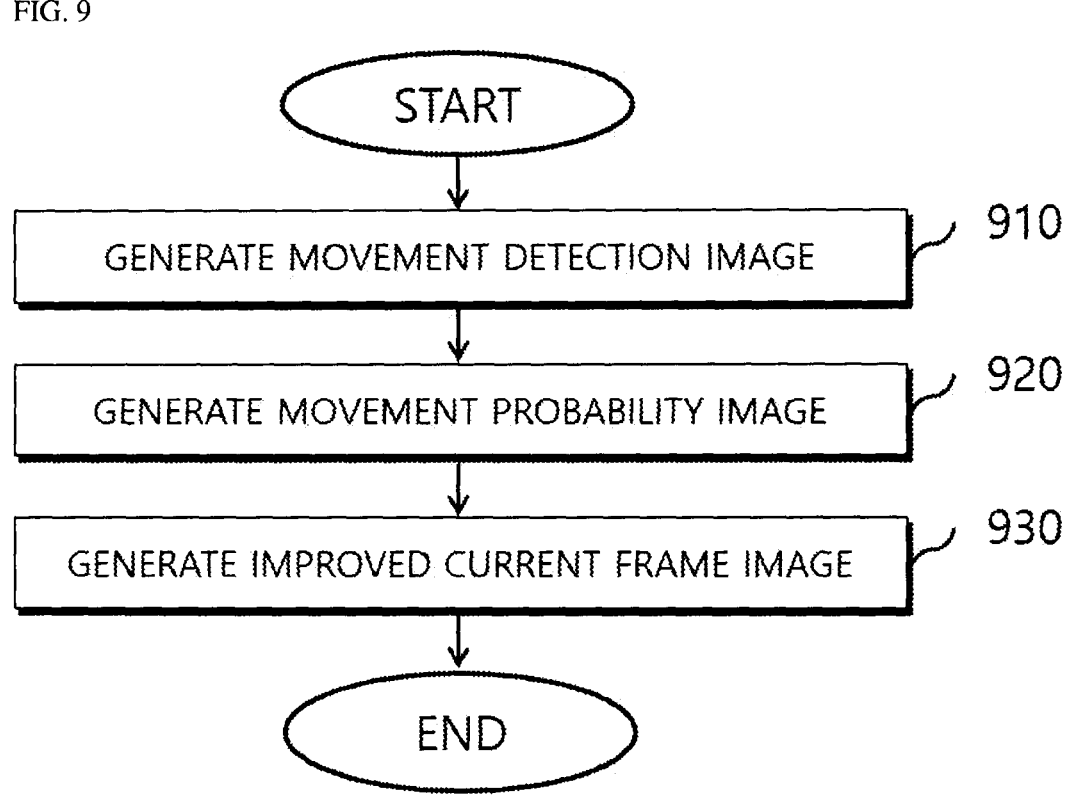
FIG. 9 is a flowchart illustrating an operation of the radiographic imaging apparatus according to one embodiment of the present disclosure.
Figure 10:
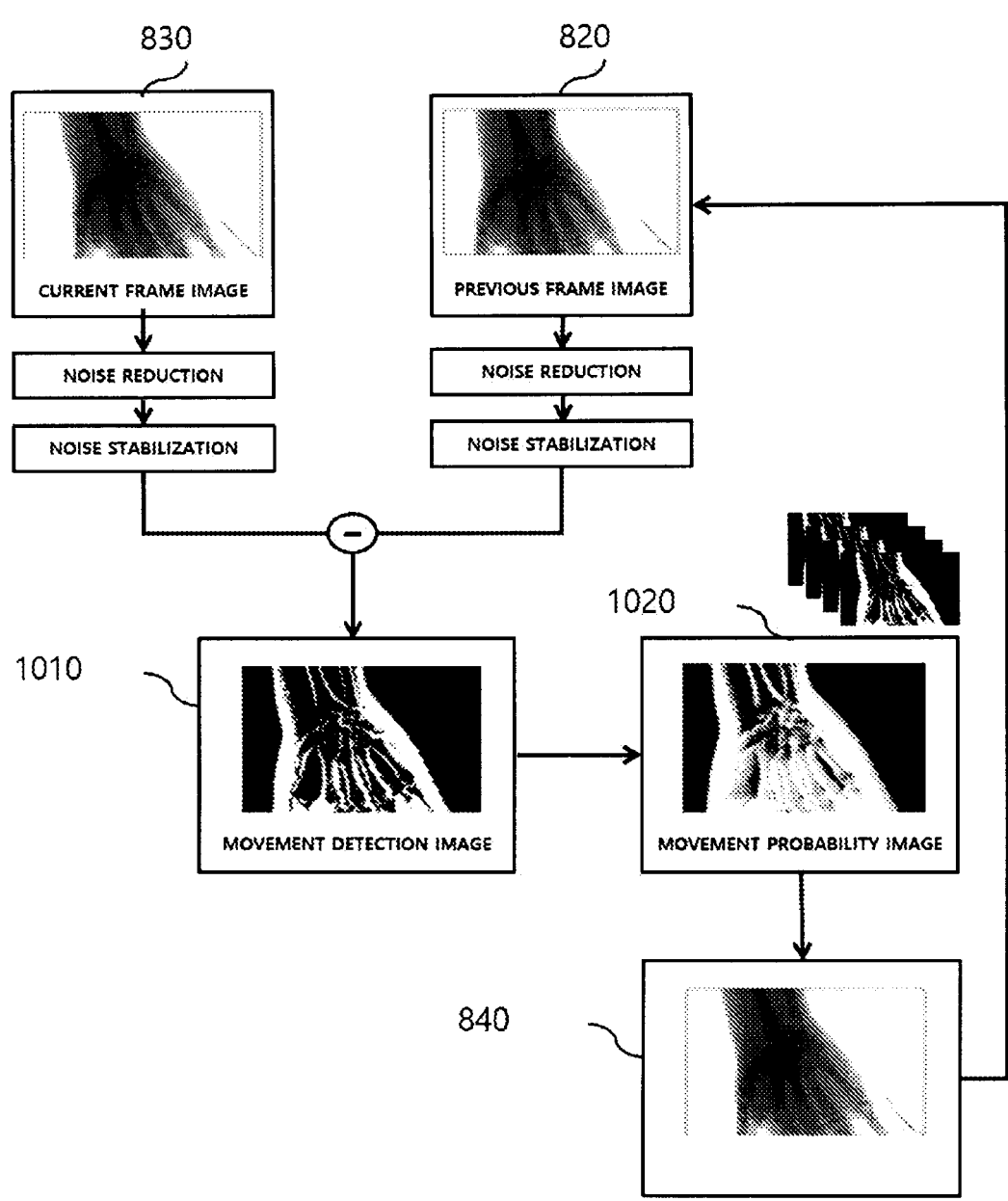
FIG. 10 is a view for describing an operation of the radiographic imaging apparatus according to one embodiment of the present disclosure.
Figure 11:
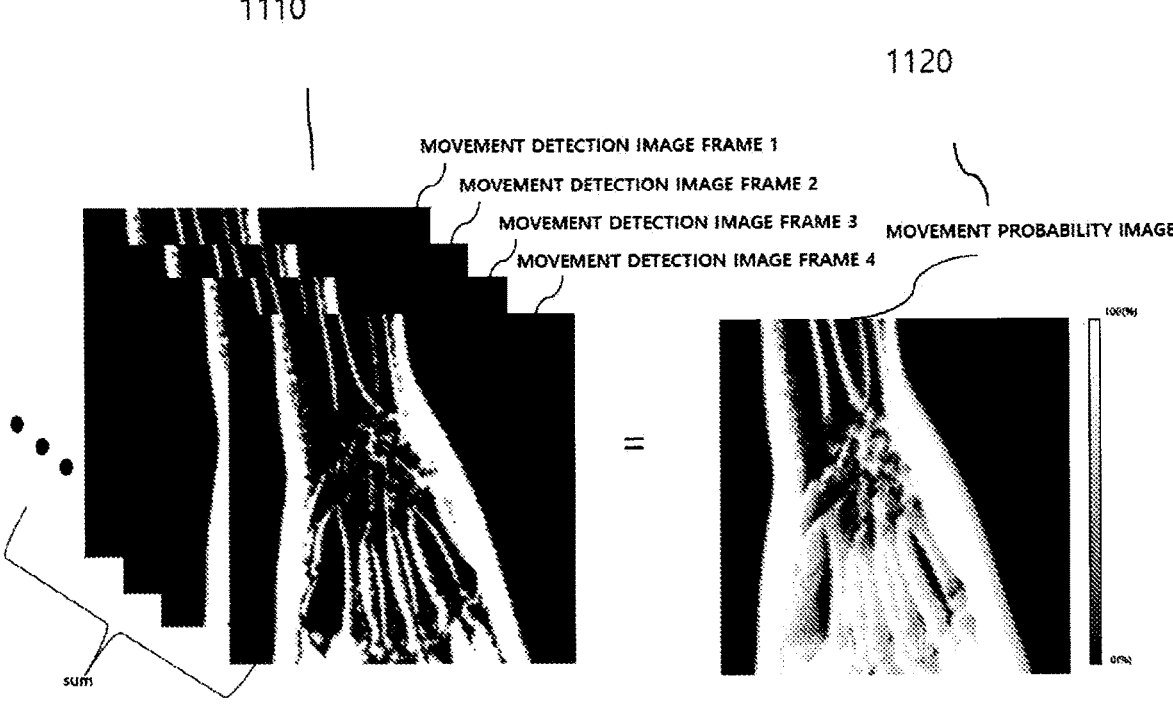
FIG. 11 is a view for describing an operation of the radiographic imaging apparatus according to one embodiment of the present disclosure.
Figure 12:
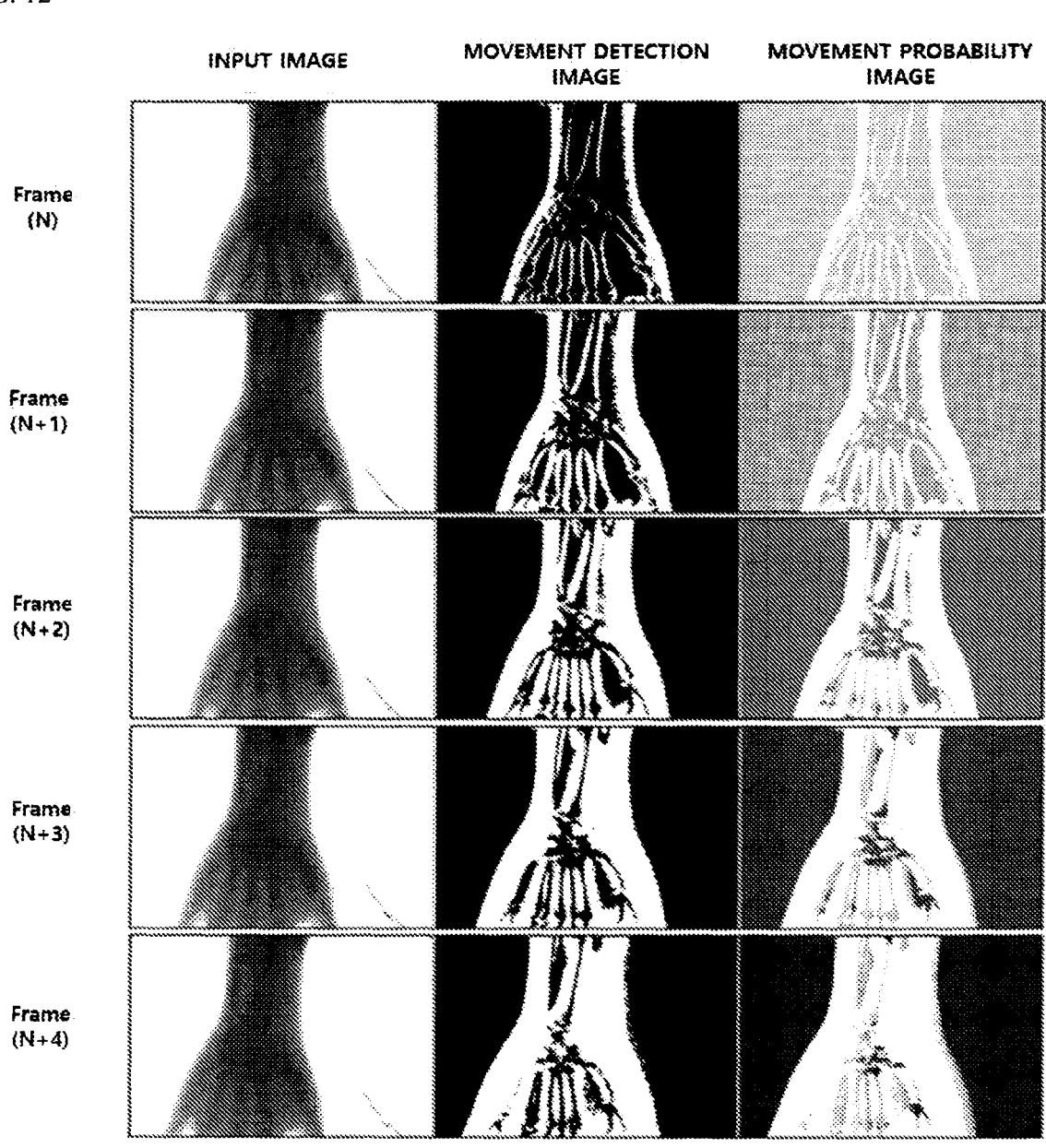
FIG. 12 is a view for describing an operation of the radiographic imaging apparatus according to one embodiment of the present disclosure.

FIG. 9 is a flowchart illustrating an operation of the radiographic imaging apparatus according to one embodiment of the present disclosure. FIG. 10 is a view for describing an operation of the radiographic imaging apparatus according to one embodiment of the present disclosure. FIG. 11 is a view for describing an operation of the radiographic imaging apparatus according to one embodiment of the present disclosure. FIG. 12 is a view for describing an operation of the radiographic imaging apparatus according to one embodiment of the present disclosure.

The operations shown in FIGS. 9 to 12 may be performed by the image postprocessor 207 included in the controller 200. The image postprocessor 207 may output an improved radiographic image with high quality by correcting the first radiographic image or the third radiographic image obtained using software, instead of controlling the radiation irradiator 111.

The image postprocessor 207 included in the controller 200 may further perform the following process when performing the obtaining of the third radiographic image (390).

Referring to FIG. 9, the controller 200 may perform generating a movement detection image including movement detection information on each pixel of a differential image obtained from a differential of a current frame image included in the third radiographic image and a previous frame image included in the third radiographic image (910).

More specifically, referring to FIG. 10 along with FIG. 9, the controller 200 may generate the movement detection image through threshold value processing of the differential image. By this, as illustrated in FIG. 10, a movement detection image 1010 may be generated from the current frame image 830 and the previous frame image 820 in which noise processing is performed. Here, the movement detection image 1010 may be obtained based on a subtraction image obtained by subtracting the previous frame image 820 from the current frame image 830.

The controller 200 generates a differential image from a differential of the current frame image 830 and the previous frame image 820 in which noise processing, that is, noise reduction and noise stabilization processing, is performed. To reduce noise, the controller 200 may add up absolute values of pixel value differences between a central pixel, which is a target of noise reduction, and any two pixels among an upper left pixel, an upper pixel, an upper right pixel, a left pixel, a right pixel, a lower left pixel, a lower pixel, and a lower right pixel adjacent to the central pixel to obtain a sum of the absolute values of the differences. The selected adjacent pixels may be appropriately determined according to necessary and required conditions. For example, a sum of absolute values of pixel value differences between the central pixel and two of the upper left pixel, the upper pixel, the upper right pixel, the left pixel, the right pixel, the lower left pixel, the lower pixel, and the lower right pixel based on the central pixel is calculated.

For example, the controller 200 may obtain a sum A1 of absolute values of a difference between a pixel value of the central pixel and a pixel value of the upper left pixel and a difference between the pixel value of the central pixel and a pixel value of the upper pixel, a sum A2 of absolute values of the difference between the pixel value of the central pixel and the pixel value of the upper left pixel and a difference between the pixel value of the central pixel and a pixel value of the upper right pixel, a sum A3 of absolute values of the difference between the pixel value of the central pixel and the pixel value of the upper left pixel and a difference between the pixel value of the central pixel and a pixel value of the left pixel, a sum A4 of absolute values of the difference between the pixel value of the central pixel and the pixel value of the upper left pixel and a difference between the pixel value of the central pixel and a pixel value of the right pixel, a sum A5 of absolute values of the difference between the pixel value of the central pixel and the pixel value of the upper left pixel and a difference between the pixel value of the central pixel and a pixel value of the lower left pixel, a sum A6 of absolute values of the difference between the pixel value of the central pixel and the pixel value of the upper left pixel and a difference between the pixel value of the central pixel and a pixel value of the lower pixel, and a sum A7 of absolute values of the difference between the pixel value of the central pixel and the pixel value of the upper left pixel and a difference between the pixel value of the central pixel and a pixel value of the lower right pixel. The controller 200 may obtain a sum A8 of absolute values of the difference between the pixel value of the central pixel and the pixel value of the upper pixel and the difference between the pixel value of the central pixel and the pixel value of the upper right pixel, a sum A9 of absolute values of the difference between the pixel value of the central pixel and the pixel value of the upper pixel and the difference between the pixel value of the central pixel and the pixel value of the left pixel, a sum A10 of absolute values of the difference between the pixel value of the central pixel and the pixel value of the upper pixel and the difference between the pixel value of the central pixel and the pixel value of the right pixel, a sum A11 of absolute values of the difference between the pixel value of the central pixel and the pixel value of the upper pixel and the difference between the pixel value of the central pixel and the pixel value of the lower left pixel, a sum A12 of absolute values of the difference between the pixel value of the central pixel and the pixel value of the upper pixel and the difference between the pixel value of the central pixel and the pixel value of the lower pixel, and a sum A13 of absolute values of the difference between the pixel value of the central pixel and the pixel value of the upper pixel and the difference between the pixel value of the central pixel and the pixel value of the lower right pixel. By the above process, the controller 200 may determine the sums of absolute values of pixel value differences between the central pixel and the pixels around the central pixel. That is, the controller 200 may obtain sums A1 to A29 of absolute values by the above process. Here, pixels further in a direction in which a sum Ak of absolute values is smaller may be viewed as pixels having the most similar directionality as the central pixel. For example, when A1 is the smallest among A1 to A29, the upper left pixel and the upper pixel may be selected, and a direction sequentially progressing to the upper left pixel, the central pixel, and the upper pixel may be selected.

Since impulse noise may be seen as a pixel having an especially greater absolute value than surrounding pixels, in order to exclude the pixel, the controller 200 may correct the pixel value of the central pixel using pixel values of two adjacent pixels having the smallest sum of absolute values of pixel value differences between the central pixel and the selected two adjacent pixels and may update the pixel value of the central pixel to a pixel value with reduced noise. For example, the controller 200 may substitute the pixel value of the central pixel with a mean value or a median value of the pixel value of the central pixel and the pixel values of the selected two pixels. By performing the updating of the pixel value of the central pixel in this way sequentially while shifting a mask, noise reduction through pixel value update may be performed.

Although an embodiment in which pixels around the central pixel in a single frame are taken into consideration has been described above, the present disclosure is not limited thereto. The controller 200 may further use at least one of a just-before frame and a just-after frame of the current frame. The just-after frame is an image obtained by the image obtainer 112 and may be a frame obtained right after the current frame. The current frame may be a frame in which noise processing is in progress, and the just-after frame may be a frame in which noise processing has not been performed yet. The just-before frame is a frame right before the current frame and may be a frame in which noise processing is complete.

The controller 200 may obtain an absolute value of a pixel value difference between the central pixel of the current frame and at least one of a central pixel of the just-before frame at the same position as the central pixel of the current frame and any of an upper left pixel, an upper pixel, an upper right pixel, a left pixel, a right pixel, a lower left pixel, a lower pixel, and a lower right pixel adjacent thereto. Also, the controller 200 may also obtain an absolute value of a pixel value difference between the central pixel of the current frame and at least one of a central pixel of the just-after frame at the same position as the central pixel of the current frame and any of an upper left pixel, an upper pixel, an upper right pixel, a left pixel, a right pixel, a lower left pixel, a lower pixel, and a lower right pixel adjacent thereto. The controller 200 may select two pixels having the smallest sum of two absolute values. The controller 200 may substitute the pixel value of the central pixel of the current frame with a mean value or a median value of the pixel value of the central pixel of the current frame and the pixel values of the selected two pixels.

The controller 200 may stabilize noise by reducing noise variance between the current frame image and the previous frame image in which noise is reduced. For example, since the amount of photons incident on each sensor to obtain a radiographic image is random and independent, instead of being constant over time, the noise characteristic of the radiographic image typically follows a Poisson distribution. In an embodiment of the present disclosure, in order to remove noise having the Poisson distribution characteristic, noise is approximated to noise having a Gaussian distribution characteristic through an Anscombe transform. Since the Anscombe transform is an approximation to a Gaussian distribution close to Standard Deviation 1, transformed data has stable noise variance.

The controller 200 may generate a differential image by calculating a pixel value difference between pixels at the same position for all pixels of the current frame image 830 and the previous frame image 820. The differential image may include subject movement information and residual noise information. In addition, the differential image may be stabilized by using a mean value filter, a media value filter, or the like on the generated differential image.

The controller 200 may determine a threshold pixel value for movement detection of the differential image and perform threshold value processing based on the determined threshold pixel value to detect the movement presence/absence of each pixel and generate the movement detection image 1010 according thereto. When the threshold pixel value for movement detection is set too low, movement detection sensitivity may become high, and a noise reduction level may be low, and conversely, when the threshold pixel value is set too high, the movement detection sensitivity may become low, and motion blur (a drag phenomenon) may occur. Since X-ray images are obtained under different dose conditions and subject characteristics, it is difficult to predict pixel values of the obtained images, and it is necessary to set an appropriate threshold pixel value according to the pixel values.

The controller 200 according to an embodiment of the present disclosure may apply an adaptive threshold pixel value whose size changes according to the size of a pixel value of each pixel of the differential image. For example, the threshold pixel value for movement determination may be set to gradually decrease with an increase in the pixel values of the pixels.

Due to the controller 200, when an absolute value of a pixel value of a pixel included in the differential image is greater than or equal to a predetermined threshold pixel value, a pixel value of a corresponding pixel included in the movement detection image 1010 may be "0," and when an absolute value of a pixel value of a pixel included in the differential image is less than the predetermined threshold pixel value, a pixel value of a corresponding pixel included in the movement detection image 1010 may be "1." However, the present disclosure is not limited thereto, and due to the controller 200, when an absolute value of a pixel value of a pixel included in the differential image is greater than or equal to a predetermined threshold pixel value, a pixel value of a corresponding pixel included in the movement detection image 1010 may be "1," and when an absolute value of a pixel value of a pixel included in the differential image is less than the predetermined threshold pixel value, a pixel value of a corresponding pixel included in the movement detection image 1010 may be "0."

The movement detection image 1010 may include information on the movement presence/absence of each pixel. For example, a pixel with movement may be set to have a value of "0," and a pixel without movement may be set to have a value of "1." That is, all the pixels of the movement detection image 1010 may have a pixel value of 0 or 1, pixels having a value of 0 may indicate pixels with movement based on the previous frame image, and pixels having a value of 1 may indicate pixels without movement based on the previous frame image. However, the present disclosure is not limited thereto.

The controller 200 may generate the improved current frame image 840 based on the movement detection image 1010. As described above with reference to FIG. 8, the controller 200 may perform the generating of the improved current frame image 840 by accumulating and averaging the pixel values included in at least a part of the current frame image 830 included in the third radiographic image and the pixel values included in at least a part of the previous frame image 820 included in the third radiographic image. Here, the controller 200 may further use the movement detection image 1010. More specifically, the controller 200 may determine pixel values of the current frame image 830 as pixel values of the improved current frame image 840 for pixels whose movement is detected in the movement detection image 1010 and may determine pixel values of the improved current frame image 840 by accumulating and averaging pixel values of the current frame image 830 and pixel values of the previous frame image 820 for pixels whose movement is not detected. However, the present disclosure is not limited thereto, and the controller 200 may also use a movement probability image instead of the movement detection image 1010 to generate the improved current frame image 840.

Referring back to FIG. 9, the controller 200 may perform generating a movement probability image based on the generated movement detection image and a movement detection image accumulated up to a previous frame (920).

Referring to FIGS. 9 and 10, the controller 200 may generate a movement probability image 1020 by accumulating movement detection images in chronological order in a separate memory based on a movement detection result. The movement probability image 1020 may be used to determine an appropriate mixing ratio of the previous frame image 820 and the current frame image 830 for generating the improved current frame image 840. As described above, the previous frame image 820 may include at least one frame. The current frame image 830 may include one frame.

The controller 200 may perform the following process to perform the generating of the movement probability image (920). The controller 200 may perform the generating of the movement probability image 1020 from a sum of the movement detection image 1010 of the current frame and one or more movement detection images up to the previous frame.

More specifically, FIG. 11 is a view showing a method of generating the movement probability image 1020 using the movement detection image 1010. The controller 200 may cumulatively store the movement detection image 1010 obtained through movement detection in chronological order for each frame in a separate independent memory to generate and update the movement probability image 1020. The left image of FIG. 11 shows cumulatively stored movement detection images 1110, and the right image shows a movement probability image 1120 obtained from the sum of the movement detection images. The movement probability image 1120 of the current frame may be generated from a sum of values of the same pixels of the movement probability image of the previous frame and the movement detection image 1010 of the current frame. That is, the movement probability image 1120 of a specific frame is an image obtained from a sum of pixel values of the same pixels of all the movement detection images obtained up to the corresponding frame. For example, referring to FIG. 11, when the current frame is the fourth frame, the sum of values of the same pixels in movement detection images obtained up to the current fourth frame become values of the same pixels of a movement probability image of the current frame.

When values of pixels determined to have movement in the movement detection images are set as "0" and shown bright, and values of pixels determined to not have movement are set as "1" and shown dark, pixels of the movement probability image each have a value corresponding to a sum of movement detection values (0 or 1) of the corresponding pixel and have different values, that is, different brightness, according to the number of movement determinations. For example, when it is assumed that a movement probability image consists of ten frames, the corresponding movement probability image is obtained from the sum of ten movement detection images, and each pixel of the movement probability image has any one value between 0 and 10. Here, when all of the values of the same pixels of all the movement detection images are 0, the corresponding pixel of the movement probability image has a value of 0, and when all of the values of the same pixels of all the movement detection images are 1, the corresponding pixel of the movement probability image has a value of 10. By this, as illustrated in FIG. 10, each pixel of the movement probability image has a pixel value, that is, brightness, according to the number of movement detections of the same pixel of the movement detection images up to the corresponding frame.

In this sense, it may be seen that movement probability is higher as a pixel value is brighter, and the movement probability is lower as a pixel value is darker in the generated movement probability image 1020. For example, movement probability becomes higher when movement is detected while frames progress in chronological order at the same pixel position, and the movement probability becomes lower when movement is not detected.

The value of each pixel of the movement probability image 1020 indicates a degree of movement and a movement probability value of the corresponding pixel. That is, when a determination value of "0" is assigned when there is movement, and a determination value of "1" is assigned when there is no movement, it indicates that the movement probability of the corresponding pixel is higher as the pixel value of the movement probability image 1020 is smaller.

An example of a process of generating the movement detection image 1010 and the movement probability image 1020 according to an input image as frames progress is illustrated in FIG. 12. The movement detection image may be generated from a differential of a frame image and a previous frame image of each frame, and the movement probability image 1020 may be generated from the sum of the movement detection image and a movement detection image of a previous frame.

Referring to FIG. 9, the controller 200 may perform generating an improved current frame image by mixing the current frame image and the previous frame image based on the movement probability image (930).

In order to perform the generating of the improved current frame image (930), the controller 200 may perform variably determining a mixing ratio of the current frame image 830 and the previous frame image 820 according to a value indicating a degree of movement of each pixel of the movement probability image 1020. Also, the controller 200 may determine the mixing ratio for a reflection rate of the current frame image relative to the previous frame image to increase as the degree of movement indicated by the value of each pixel of the movement probability image 1020 is higher.

Here, the current frame image 830 may be a current frame image in which noise is reduced by the controller 200, and the previous frame image 820 may be a previous frame image in which noise is reduced by the controller 200. Also, the previous frame image 820 may be a previously improved frame image or an unimproved frame image. Here, the controller 200 may generate the improved current frame image 840 by mixing the current frame image 830 and the previous frame image 820 in an appropriate mixing ratio based on the movement probability image 1020. That is, the controller 200 may obtain a weighted average of the current frame image 830 and the previous frame image 820 based on the movement probability image 1020.

The reflection rate of the current frame image 830 may be set to increase relative to an increase in the degree to which the value of each pixel of the movement probability image 1020 indicates movement. That is, the mixing ratio may be determined for a weighted value of the current frame image 830 to increase with an increase in the movement probability determined by the pixel values included in the movement probability image 1020. For example, the reflection rate may be determined so that the reflection rate of the current frame image 830 linearly increases with an increase in the degree to which the pixel values of the movement probability image 1020 indicate movement in pixel units.

As a specific example, for a pixel with a large amount of movement, a predetermined weighted value α1, for example, 0.8, may be imparted to the corresponding pixel of the current frame image 830, a weighted value (1−α1), for example, a weighted value of 0.2, may be imparted to the corresponding pixel of the previous frame image 820, and such a mixing process may be performed for all the pixels.

Meanwhile, the current frame image 830 and the previous frame image 820 may be mixed by, for a pixel with a small amount of movement, imparting a predetermined weighted value α2, for example, 0.2, to the corresponding pixel of the current frame image 830 and imparting a weighted value (1−α2), for example, a weighted value of 0.8, to the corresponding pixel of the previous frame image 820. An image without motion blur may be obtained when a weighted value of the current frame image 830 becomes higher for a pixel with a large amount of movement. Consequently, in the improved current frame image 840, based on the movement probability, a pixel with a large amount of movement may be updated by reflecting a value of the current frame more, and a pixel with a small amount of movement may be updated by reflecting a value of the previous frame more, and in this way, noise reduction performance may be improved as frames accumulate over time.

Various embodiments have been described above. Those of ordinary skill in the art to which the present disclosure pertains should understand that the present disclosure may be implemented in modified forms within the scope not departing from essential characteristics of the present disclosure. Therefore, the embodiments disclosed herein should be considered in an illustrative aspect instead of a limiting aspect. The scope of the present disclosure is shown by the claims rather than the above description, and all differences present within the scope equivalent to the claims should be construed as being included in the present disclosure.

Meanwhile, the above-described embodiments of the present disclosure may be written by a program that may be executed by a computer, and may be implemented by a universal digital computer operating a program using computer-readable recording media. The computer-readable recording media include storage media such as magnetic storage media (for example, a ROM, a floppy disk, a hard disk, and the like) and optical readable media (for example, a compact disc (CD)-ROM, a digital versatile disc (DVD), and the like).

What is claimed is:

1. A radiographic imaging apparatus comprising:
an image outputter outputting a first radiographic image included in continuous radiographic images obtained by radiographic imaging of a subject;
an image brightness information extractor obtaining brightness information from the first radiographic image;
a first irradiation condition calculator determining a first irradiation condition based on the brightness information;
an irradiation controller controlling a radiation dose based on the first irradiation condition;
a second irradiation condition calculator determining a second irradiation condition based on a second radiographic image generated based on the first irradiation condition when an imaging site of the subject is fixed; and
a dose reducer reducing or maintaining the radiation dose based on the second irradiation condition.

2. The radiographic imaging apparatus of claim 1, wherein a value resulting from subtracting the radiation dose based on the second irradiation condition from the radiation dose based on the first irradiation condition is less than or equal to 70% of the dose based on the first irradiation condition.

3. The radiographic imaging apparatus of claim 1, wherein the first irradiation condition calculator is deactivated when the dose is reduced by the dose reducer.

4. The radiographic imaging apparatus of claim 1, wherein an improved current frame image is generated by accumulating and averaging pixel values included in a current frame image included in a third radiographic image output using the dose reduced by the dose reducer and a previous frame image included in the third radiographic image.

5. The radiographic imaging apparatus of claim 1, further comprising an image postprocessor postprocessing a third radiographic image output using the dose reduced by the dose reducer,
wherein the image postprocessor adjusts at least one of brightness information and contrast information of the third radiographic image to be similar to at least one of brightness information and contrast information of the second radiographic image.

6. An operation method of a radiographic imaging apparatus including a radiation irradiator irradiating a subject with radiation, an image obtainer generating continuous radiographic images by receiving the radiation radiated from the radiation irradiator and passing through the subject, and a controller controlling the radiation irradiator and the image obtainer, the operation method comprising, by the controller:
obtaining brightness information based on a first radiographic image included in the continuous radiographic images;
determining a first irradiation condition based on the brightness information according to a first algorithm;
controlling a radiation dose based on the first irradiation condition;
obtaining a second radiographic image included in the continuous radiographic images and generated based on the first irradiation condition;
obtaining movement presence/absence information indicating whether an imaging site of the subject is fixed;
determining a second irradiation condition based on the second radiographic image according to a second algorithm when the movement presence/absence information indicates that the imaging site of the subject is fixed;
controlling the radiation dose based on the second irradiation condition; and
obtaining a third radiographic image included in the continuous radiographic images and generated based on the second irradiation condition.

7. The operation method of claim 6, wherein the radiation dose based on the second irradiation condition is greater than or equal to 30% of the radiation dose based on the first irradiation condition.

8. The operation method of claim 6, wherein the first algorithm determining the first irradiation condition and the second algorithm determining the second irradiation condition are different from each other.

9. The operation method of claim 6, wherein the obtaining of the third radiographic image includes generating an improved current frame image by accumulating and averaging pixel values included in at least a part of a current frame image included in the third radiographic image and pixel values included in at least a part of a previous frame image included in the third radiographic image.

10. The operation method of claim 6, wherein the obtaining of the third radiographic image includes:

generating a movement detection image including movement detection information on each pixel of a differential image obtained from a differential of a current frame image included in the third radiographic image and a previous frame image included in the third radiographic image;

generating a movement probability image based on the generated movement detection image and a movement detection image accumulated up to a previous frame; and generating an improved current frame image by mixing the current frame image and the previous frame image based on the movement probability image.

11. The operation method of claim 10, wherein:

the generating of the movement probability image includes, generating the movement probability image from a sum of the movement detection image of the current frame and one or more movement detection images up to the previous frame;

the generating of the improved current frame image includes variably determining a mixing ratio of the current frame image and the previous frame image according to a value indicating a degree of movement of each pixel of the movement probability image; and the mixing ratio is determined for a reflection rate of the current frame image relative to the previous frame image to increase as the degree of movement indicated by the value of each pixel of the movement probability image is higher.

12. The operation method of claim 6, wherein:

the obtaining of the brightness information includes, obtaining the brightness information by averaging pixel values included in at least a part of the first radiographic image; and the determining of the first irradiation condition includes, determining the first irradiation condition for the brightness information to increase when the brightness information is less than predetermined first threshold brightness information and determining the first irradiation condition for the brightness information to decrease when the brightness information is greater than the predetermined first threshold brightness information.

13. The operation method of claim 12, wherein the obtaining of the brightness information by averaging the pixel values included in at least a part of the first radiographic image includes:

obtaining a region showing the subject from the first radiographic image based on a subject region obtaining model; and obtaining the brightness information by averaging pixel values included in the region showing the subject.

14. The operation method of claim 6, wherein the determining of the second irradiation condition includes:

obtaining a downsampled image by downsampling the second radiographic image into units of patches of a predetermined size;

obtaining a minimum pixel value among pixel values included in the downsampled image; and determining the second irradiation condition for the minimum pixel value to become equal to predetermined second threshold brightness information when the minimum pixel value is greater than the second threshold brightness information.

15. The operation method of claim 14, wherein the determining of the second irradiation condition for the minimum pixel value to become equal to the second threshold brightness information includes:

determining a reduction rate based on the minimum pixel value and the second threshold brightness information; and determining the second irradiation condition for the radiation irradiator to radiate radiation with a dose resulting from subtracting a value obtained by multiplying the dose based on the first irradiation condition by the reduction rate from the dose based on the first irradiation condition, wherein the reduction rate is greater than 0 and less than a predetermined maximum reduction rate.

16. The operation method of claim 6, wherein the obtaining of the movement presence/absence information includes:

determining the movement presence/absence information to indicate that the imaging site of the subject is not fixed when less than a predetermined threshold amount of time has passed from a time at which at least one of the first radiographic image and the second radiographic image was obtained; and determining the movement presence/absence information to indicate that the imaging site of the subject is fixed when the predetermined threshold amount of time or more has passed from the time at which at least one of the first radiographic image and the second radiographic image was obtained.

* * * * *